(12) United States Patent
Maekawa et al.

(10) Patent No.: US 6,398,506 B1
(45) Date of Patent: Jun. 4, 2002

(54) CENTRIFUGAL FLUID PUMP AND CONTROL DEVICE FOR OPERATING THE SAME

(75) Inventors: Jun Maekawa, Kanagawa; Takayoshi Ozaki, Shizuoka, both of (JP)

(73) Assignees: Terumo Kabushiki Kaisha, Tokyo; NTN Corporation, Osaka, both of (JP)

( * ) Notice: Subject to any disclaimer, the term of this patent is extended or adjusted under 35 U.S.C. 154(b) by 57 days.

(21) Appl. No.: 09/625,046

(22) Filed: Jul. 24, 2000

(30) Foreign Application Priority Data

Jul. 23, 1999 (JP) ............................. 11-209879
Jul. 7, 2000 (JP) ...................... 2000-206041

(51) Int. Cl.[7] ............................................ F04B 49/00
(52) U.S. Cl. ........................................ 417/12; 417/44.1
(58) Field of Search ........................... 417/423.12, 420, 417/44.1, 12

(56) References Cited

U.S. PATENT DOCUMENTS 6,184,640 B1 * 2/2001 Kawashima ................ 318/461
6,254,353 B1 * 7/2001 Polo et al. ................ 417/44.11
6,323,614 B1 * 11/2001 Palazzolo et al. ........... 318/560

* cited by examiner

*Primary Examiner*—Charles G. Freay
*Assistant Examiner*—William H. Rodriguez
(74) *Attorney, Agent, or Firm*—Burns, Doane, Swecker & Mathis, LLP

(57) ABSTRACT

A centrifugal fluid pump assembly includes a centrifugal fluid pump and a control device. The centrifugal fluid pump comprises a pump section including a housing and an impeller having a first magnetic material and a second magnetic material and accommodated for rotation in the housing and without contacting the housing, an impeller rotational torque generating section including a rotor having a magnet for attracting the first magnetic material of the impeller and a motor for rotating the rotor, and an impeller position control section having an electromagnet for attracting the second magnetic material of the impeller. The control device has a function of limiting an input of a number of rotations of the motor more than a predetermined number of rotations or limiting an input of a motor-driving current having a value more than a predetermined value.

32 Claims, 31 Drawing Sheets magnetic coupling abnormality detecting circuit second circuit for detecting abnormality of magnetic coupling second circuit for detecting abnormality of magnetic coupling second circuit for detecting abnormality of magnetic coupling circuit for determining whether motor rotates in high load-applied state circuit for determining whether motor rotates in high load-applied state circuit for detecting abnormality of magnetic bearing current

CENTRIFUGAL FLUID PUMP AND CONTROL DEVICE FOR OPERATING THE SAME

BACKGROUND OF THE INVENTION

The invention relates to a centrifugal fluid pump assembly for pumping a medical fluid, typically blood.

In recent medical treatment, centrifugal blood pumps are increasingly used in artificial heart/lung units for extracolporeal blood circulation. Centrifugal pumps of the magnetic coupling type wherein a driving torque from an external motor is transmitted to an impeller through magnetic coupling are commonly used because the physical communication between the blood chamber of the pump and the exterior can be completely excluded to prevent invasion of bacteria.

The centrifugal blood pump includes a housing having a blood inlet port and a blood outlet port and an impeller rotatable accommodated in the housing and feeding blood by a centrifugal force generated during its rotation. The impeller is having magnetic materials (permanent magnet) disposed therein is rotated by a rotor having magnets for attracting the magnetic materials of the impeller thereto and by a rotational torque generating mechanism having a motor for rotating the rotor. The impeller rotates without contacting the housing, with the impeller being attracted to the side opposite to the rotor-disposed side by a magnetic force.

In the magnet coupling-utilizing centrifugal fluid pump, there is a danger that the magnet coupling may have a power saving (in other words, decoupling between the impeller and the rotor) when a load is excessively increasingly applied to the rotating impeller and the like. when the power swing occurs, the rotation of the impeller stops.

The use of a magnet having a large magnetic force is conceivable to prevent the power swing from occurring in the magnet coupling. The impeller is capable of rotating without contacting the housing generate owing to the balance between the attractive force generated by the magnet coupling between the impeller and the rotor and an attractive force, reciprocal to the attractive force of the magnet coupling, generated by an electromagnet or the like. It is possible to prevent the occurrence of the power swing by increasing the magnetic force in the magnet coupling. But it is necessary to provide the electromagnet with high current. However, the reduction of the power consumption is an important subject in the blood pump to be implanted in the human body.

It is a first object of the invention to provide a centrifugal fluid pump assembly capable of preventing power swing from occurring in magnet coupling, namely, between an impeller and a rotor without increasing the magnetic force in the magnet coupling.

In the magnet coupling-utilizing centrifugal fluid pump, there is a danger that the magnet coupling may have a power swing when a load is excessively increasingly applied to the rotating impeller and the like. when the power swing occurs, the rotation of the impeller stops. Therefore, it is desirable to reliably grasp the occurrence of the power swing in the magnet coupling. It is also desirable for a determining function to erroneously determine a state in which the power swing has not occurred as a state in which the power swing has occurred.

It is a second object of the invention to provide a centrifugal fluid pump assembly having a power swing detection function which allows whether or not the power swing has occurred in the magnet coupling to be checked securely from outside and which rarely erroneously determines a state in which the power swing has not occurred as a state in which the power saving has occurred.

SUMMARY OF THE INVENTION

According to a first aspect of the invention, there is provided a centrifugal fluid pump assembly comprises a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device having an input portion for inputting a set number of rotations of the motor or an input portion for inputting a set motor-driving current value; and a function of limiting an input of a number of rotations of the motor more than a predetermined number of rotations or limiting an input of the motor-driving current having a value more than a predetermined value.

According to a second aspect of the invention, there is provided a centrifugal fluid plump assembly comprises a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device having an input portion for inputting a motor-driving current value or an input portion for inputting a set number-of-rotations of the motor; and a motor rotation control part having a function of storing an upper limit value of the motor-driving current and a function of limiting a supply of the motor-driving current having a value more than the stored upper limit value to the motor.

According to a third aspect of the invention, there is provided a centrifugal fluid pump assembly comprises a centrifugal fluid pump comprising a centrifugal fluid pump section inducing a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including an input portion for inputting a set number of rotations of the motor and a motor rotation control part having a function of storing an upper limit of the number of rotations of the motor; a comparing function of comparing the stored upper limit of the number of rotations of the motor, with a set number of rotations of the motor inputted at the input portion for inputting a set number of rotations of the motor; and a motor rotation control function of controlling a rotation of the motor such that the motor rotates at the set number of rotations of the motor it the set number of rotations of the motor is smaller than the upper limit of the number of rotations of the motor and such that the motor rotates at the upper limit of the number of rotations of the motor if the set number of rotations of the motor is more than the upper limit value thereof.

According to a forth aspect of the invention, there is provided a centrifugal fluid pump assembly comprises a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a detecting portion for detecting the number of rotations of the motor and a or motor rotation control part having a function of storing an tipper limit of number of rotations of the motor and a control function of controlling a rotation of the motor such that a detected number of rotations of the motor does not exceed the upper limit of the number of rotations.

According to a fifth aspect of the invention, there is provided a centrifugal fluid pump assembly comprising a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring function of monitoring electric current flowing through the electromagnet and a motor control function of controlling a rotation of the motor such that a rotational speed of the motor is reduced when an amplitude of electric current, flowing through the electromagnet, detected by the current monitoring function is more than a predetermined value.

According to a sixth aspect of the invention, there is provided a centrifugal fluid pump assembly comprises a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring function of monitoring electric current flowing through the electromagnet and a motor control function of controlling a rotation of the motor such that a rotational speed of the motor is reduced when an average of values of the electric currents, detected by the monitoring function, flowing through the electromagnet in a predetermined period of time is less than a predetermined value.

According to a seventh aspect of the invention, there is provided a centrifugal fluid pump assembly comprises a centrifugal fluid pump comprising a centrifugal fluid pump section inducing a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring function of monitoring electric current flowing through the electromagnet and a motor control function of controlling a rotation of the motor such that a rotational speed of the motor is reduced when a fall degree of the average of the values of the electric currents flowing therethrough relative to an average of values of the electric currents flowing therethrough in an early period of time after an actuation of the centrifugal fluid pump assembly exceeds a predetermined range.

According to a eighth aspect of the invention, there is provided a centrifugal fluid pump assembly comprises a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring function of monitoring electric current flowing through the electromagnet; a monitoring function of monitoring motor-driving current; a monitoring function of monitoring the number of rotations of the motor; and a function of determining whether or not the impeller has a power swing by utilizing a current value monitored by the monitoring function of monitoring the electric current flowing through the electromagnet, a value of the motor-driving current monitored by the monitoring function of monitoring the motor-driving current, and the number of rotations of the motor monitored by the monitoring function of monitoring the number of rotations thereof.

BRIEF DESCRIPTION OF THE DRAWINGS

The above and other objects, features and advantages of the invention will be better understood by reading the following description, taken in conjunction with the accompanying drawings.

DETAILED DESCRIPTION OF THE PREFERRED EMBODIMENTS

Figure 1:
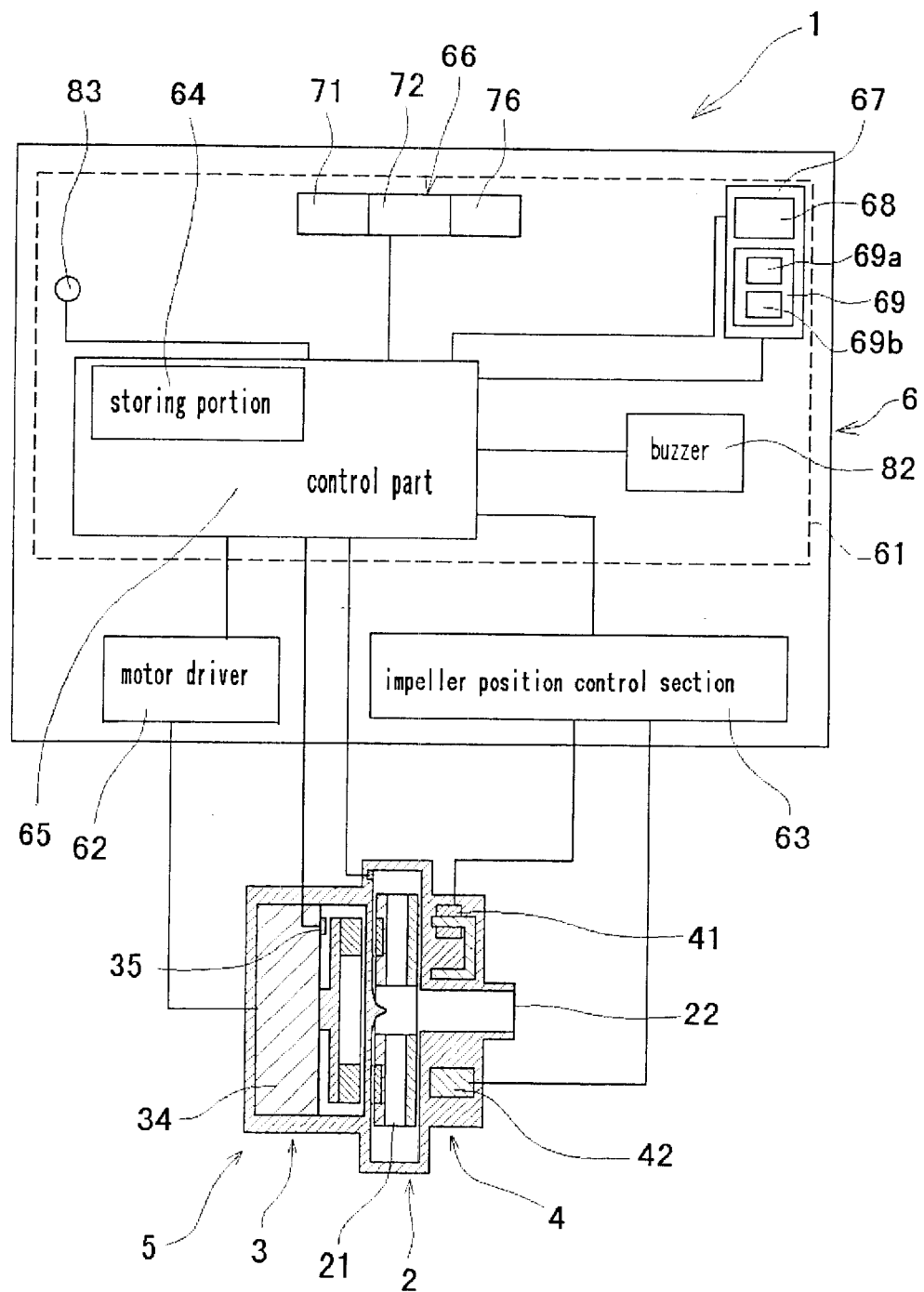
FIG. 1 is a block diagram showing an embodiment of the centrifugal fluid pump assembly of the invention.
Figure 2:
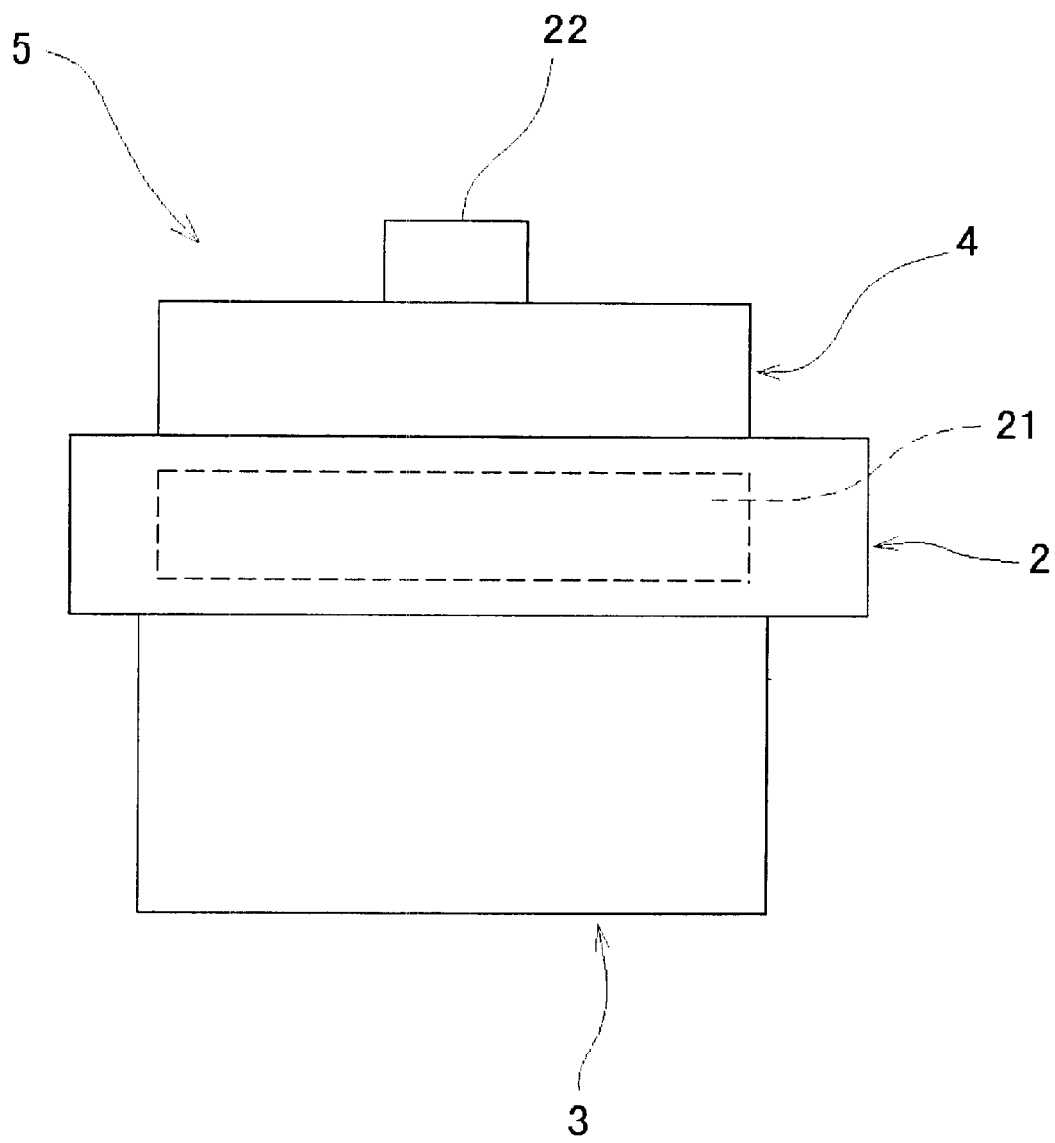
FIG. 2 is a front view showing an example of a centrifugal fluid pump that is used in the invention.
Figure 3:
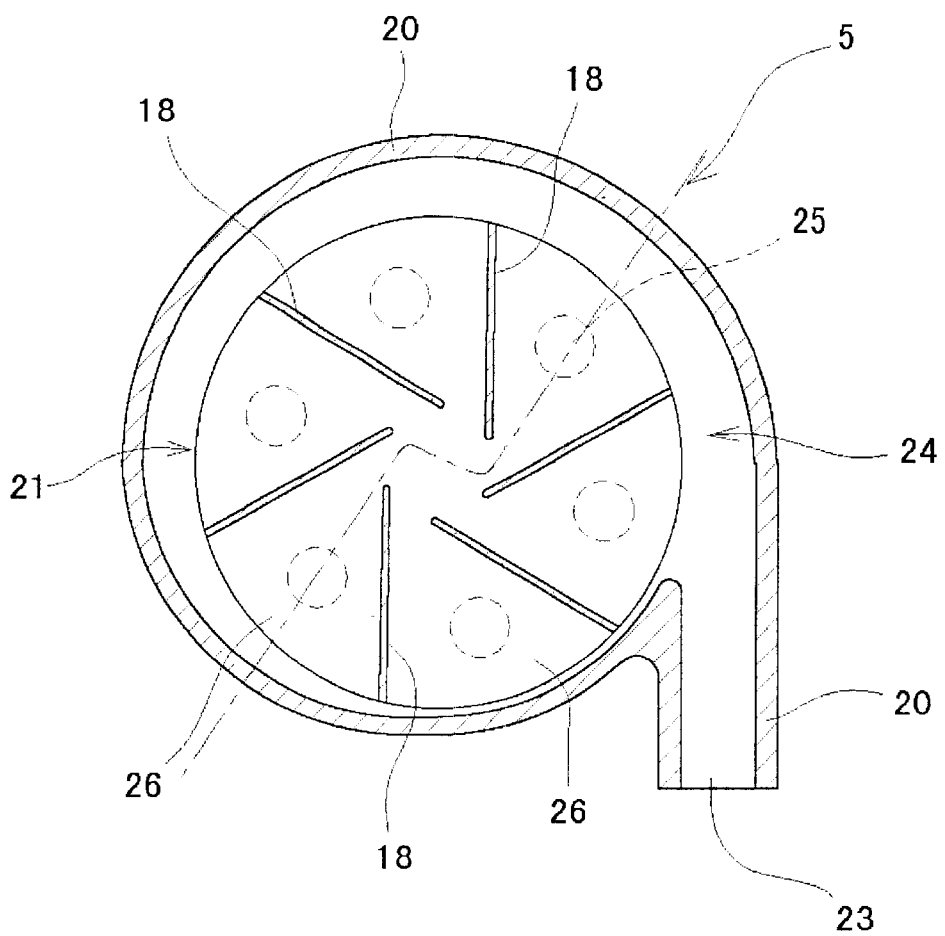
FIG. 3 is a cross-sectional view cut horizontally at the position of an impeller, showing the centrifugal fluid pump shown in FIG. 2.
Figure 4:
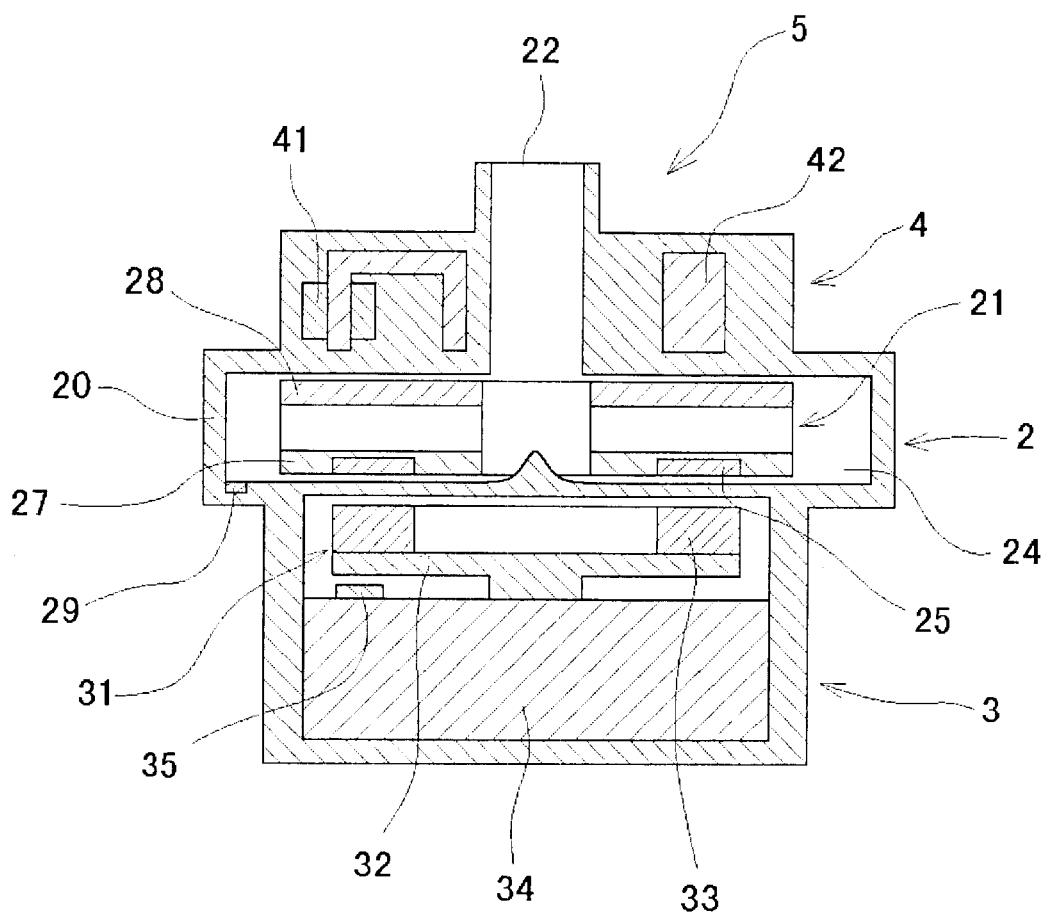
FIG. 4 is a vertical sectional view showing the centrifugal fluid pump shown in FIG. 2.
Figure 5:
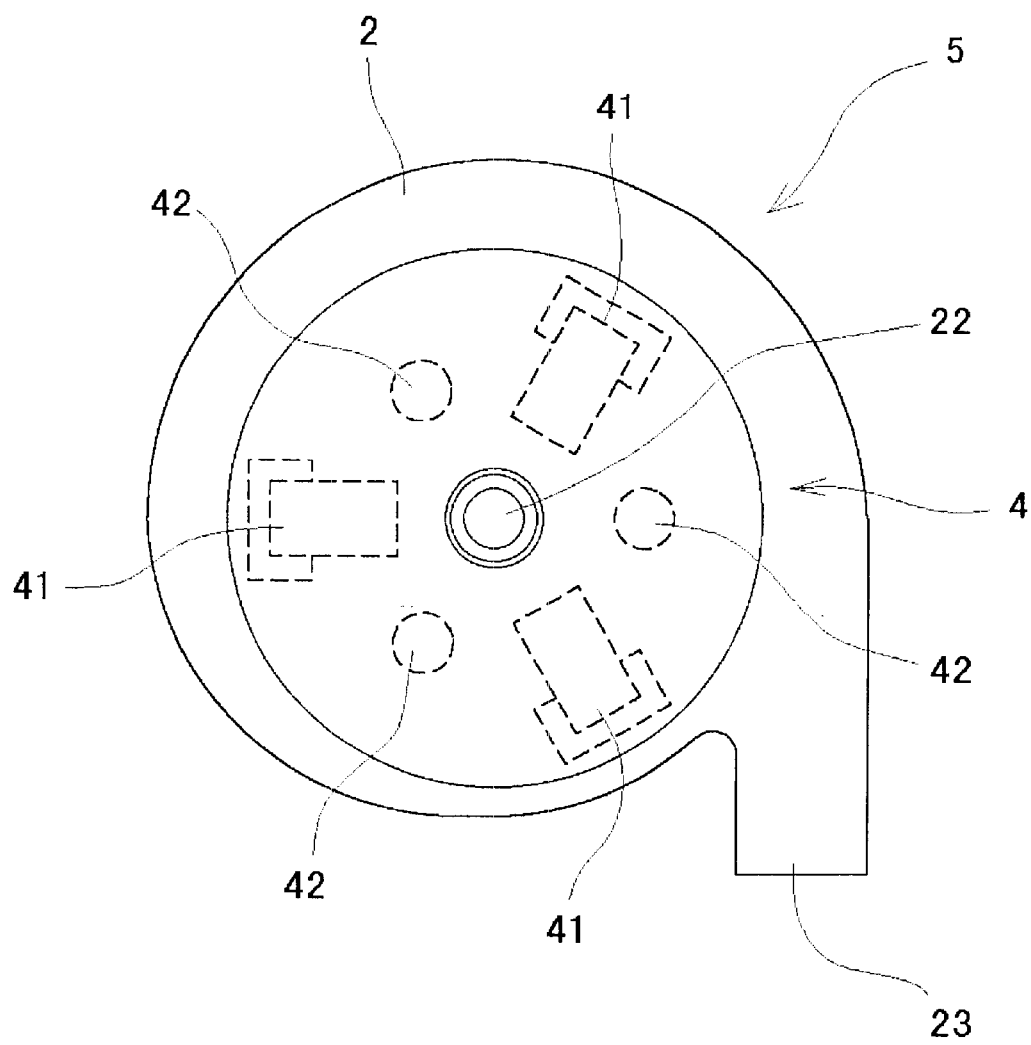
FIG. 5 is a plane view showing the centrifugal fluid pump shown in FIG. 2.

An embodiment of the centrifugal fluid pump assembly according to the invention applied to a blood pump is described below with reference to the accompanying drawings.

A centrifugal fluid pump assembly 1 of the invention includes a centrifugal fluid pump 5 and a control device 6.

The centrifugal fluid pump 5 comprises a pump section 2 including a housing 20 and an impeller 21 having a first magnetic material 25 and a second magnetic material 28 and accommodated for rotation in the housing and without contacting the housing, an impeller rotational torque generating section 3 including a rotor 31 having a magnet 33 for attracting the first magnetic material 25 of the impeller 21 and a motor 34 for rotating the rotor 31, and an impeller position control section 4 having an electromagnet 41 for attracting the second magnetic material 28 of the impeller 21.

Figure 6:
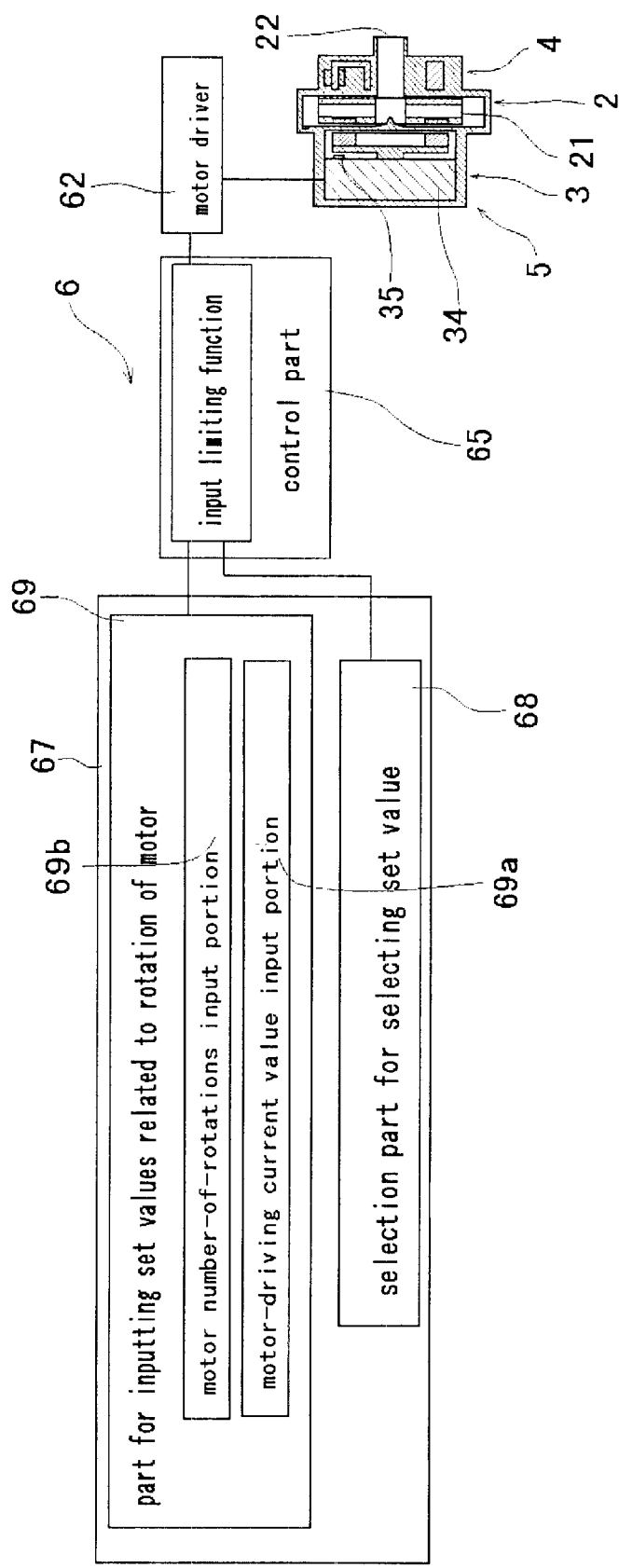
FIG. 6 is a block diagram showing the embodiment of the centrifugal fluid pump assembly of the invention.

As shown in FIGS. 1 and 6, the control device 6 has a portion 69a for inputting a set motor-driving current value (hereinafter referred to as set motor-driving current input portion 69a) or/and a portion 69b for inputting a set number of rotations of the motor (hereinafter referred to as set motor number-of-rotations input portion 69b) and an input limiting function for limiting an input of a number of rotations of the motor more than a predetermined one or/and limiting an input of the motor-driving current having a value more than a predetermined one. The control device 6 has an input mode selection part 68 for selecting the input of the set motor-driving current value or the input of the set number of rotations of the motor.

In the pump assembly 1 of the embodiment, the control device 6 has the set motor-driving current input portion 69a and a motor rotation control part 65. The motor rotation control part 65 has a function of storing an upper limit value of the motor-driving current and a function of limiting an input of a set motor-driving current value more than the stored upper limit value thereof. Using a liquid (for example, blood or liquid whose property is close to blood) to be fed, a motor-driving current value at which the centrifugal pump has a power swing (in other words, decoupling) is examined. The power swing means a power swing of coupling of magnetic bearing (in other words, power swing of magnetic coupling). For safety, the power swing-causing current value thus detected or a value 20–50% lower than that is set as the upper limit value of the motor-driving current. The upper limit value is stored in the storing portion 64 of the control part 65. If an operator inputs the motor-driving current having a value more than the stored upper limit value, the control part 65 issues an instruction of flashing an alarm lamp 83 on and off or ringing a buzzer 82 to inform the operator that inputting the motor-driving current value is unacceptable. Thus, the operator inputs a different current value. Because the control device 6 has the above-described function, the motor can be prevented from being driven at a motor-driving current value more than the motor-driving current value at which there may be a danger of the occurrence of the power swing. Thus, there is hardly a possibility of the occurrence of the power swing.

In addition to the above-described embodiment, the control device 6 of the pump assembly 1 may have the set motor number-of-rotations input portion 69b and the motor rotation control part 65 The motor rotation control part 65 has a function of storing an upper limit of the number of rotations of the motor and a function of limiting an input of a set number of rotations of the motor more than the stored upper limit value thereof. Using a liquid (for example, blood or liquid whose property is dose to blood) to be fed, a number of rotations of the motor at which the centrifugal pump has a power swing is examined. For safety the power swing-causing number of rotations of the motor thus detected or a value 20–50% lower than that is set as the upper limit value of the number of rotations of the motor. Tie upper limit value is stored in the storing portion 64 of the control part 65. If the operator inputs a number of rotations of the motor more than the stored upper limit value, the control part 65 issues an instruction of flashing an alarm lamp 83 on and off or ringing a buzzer 82 to inform the operator that inputting the number of rotations of the motor is unacceptable. Thus, the operator inputs a different number of rotations of the motor. Because the control device 6 has the above-described function, the motor can be prevented from being driven at number of rotations of the motor more than the number of rotations of the motor at which there may be a danger of the occurrence of the power swing. Thus, there is hardly a possibility of the occurrence of the power swing.

As shown in FIGS. 2 to 5, the centrifugal fluid pump 5 includes a centrifugal fluid pump section 2 comprising the housing 20 having the blood inlet port 22 and the blood outlet port 23 and the impeller 21 rotating inside the housing 20 to feed blood by the centrifugal force generated during its rotation, the impeller rotation torque generating section 3 (uncontrolled magnetic bearing section) for the impeller 21, arid the impeller position control section 4 (controlled magnetic bearing section) for the impeller 21.

The uncontrolled magnetic bearing section 3 and the controlled magnetic bearing section 4 cooperate such that the impeller 21 rotates while it is held in position within the housing 20.

The housing 20 has the blood inlet port 22 and the blood outlet port 23 and is formed of a non-magnetic material. The housing 20 defines therein the blood chamber 24 in fluid communication with the blood inlet and outlet ports 22 and 23. The impeller 21 is accommodated inside the housing 20. The blood inlet port 22 protrudes from near the center of the upper surface of the housing 20 in a substantially vertical direction. The blood outlet port 23 projects from a side surface of the generally cylindrical housing 20 in a tangential direction.

The disc-shaped impeller 21 having a through-hole in the center thereof is accommodated within the blood chamber 24 of the housing 20. The impeller 21 includes a disc-shaped member or a lower shroud 27 defining the lower surface thereof, an annular plate-shaped member or an upper shroud 28 defining the upper surface thereof and opening at the center thereof, and a plurality of (six in the embodiment) vanes 18 (see FIG. 3) formed between the lower and upper shrouds 27 and 28.

The vanes 18 define a corresponding plurality of (six in the embodiment) blood passages 26 between two adjacent ones and between the lower and upper shrouds.

Each blood passage 26 extends from the center opening to the outer periphery of the impeller 21 in a curved fashion. Differently stated, the vanes 18 are formed between adjacent blood passages 26. In the embodiment, the vanes 18 and blood passages 26 are respectively provided at equiangular intervals and in substantially the same shape.

A plurality of first magnetic materials 25 (six in the embodiment) are embedded in the impeller 21. The magnetic materials (for example, permanent magnets) 25 are permanent magnets and serve as follower magnets. The magnetic materials 25 are provided in the impeller 21 so that the impeller 21 is attracted away from the blood inlet port 22 by a permanent magnet 33 provided in the rotor 31 of the rotational torque generating section 3 to be described later and that the rotational torque is transmitted from the torque generating section 3 to the impeller 21. Such plural discrete magnetic materials 25 embedded in the impeller 21 ensure magnetic coupling with the rotor 31 to be described later can be ensured. Each magnetic material 25 (permanent magnet) is preferably circular in a horizontal cross section. Instead, it is possible to use a ring-shaped magnet having multi-poles (for example, 24 poles). In other words, a plurality of small magnets may be arranged in the shape of a ring such that positive and negative poles alternate with each other.

The impeller 21 further includes a second magnetic member 28 which itself constitutes an upper shroud or which is attached to the upper shroud. In the embodiment, the upper shroud in its entirety is constructed of the second magnetic member 28. The second magnetic member 28 is provided so that an electromagnet 41 of the impeller position control section 4 to be described later magnetically attracts the impeller 21 toward the blood inlet port 22. The magnetic member 28 may be formed of magnetic stainless steel, nickel or soft iron.

The impeller position control section 4 and the rotational torque generating section 3 constitute a non-contact type magnetic bearing, which magnetically attracts the impeller 21 from opposite directions to steadily hold the impeller 21 at a proper position out of contact with the inner surface of the housing 20 so that the impeller 21 may rotate within the housing 20 without contacting its inner surface.

Included in the rotational torque generating-section 3 are the housing 20, the rotor 31 accommodated in the housing 20, and a motor (whose internal structure is not shown) for rotating the rotor 31. The rotor 31 includes a rotating disc 32 and a plurality of permanent magnets 33 disposed on one surface (facing the centrifugal fluid pump section 2) of the rotating disc 32. The rotor 31 at its center is fixedly secured to the rotating shaft of the motor 34. A plurality of the permanent magnets 33 are equiangularly distributed in accordance with the arrangement mode of the permanent magnets 25 of the impeller 21. That is, the number and location of permanent magnets 33 are coincident with the number and location of the permanent magnets 25.

The impeller rotation torque generating section 3 is not limited to the illustrated one having the rotor and motor. For example, a plurality of stator coils may be used as long as it can attract the permanent magnets 25 of the impeller 21 and drive the impeller 21 for rotation.

The impeller rotation torque generating section 3 is provided with a sensor 35 for detecting the number of rotations of the motor 34 or the rotor 31. Optical or magnetic sensors can be used as the sensor 35. The number of rotations of the motor 34 or the rotor 31 may be detected by a counter electromotive force that is generated in the coil of the motor.

Included in the impeller position control section 4 are a plurality of electromagnets 41 accommodated in the housing 20 and attracting the magnetic member 28 of the impeller, 21 thereto and a plurality of position sensors 42 for detecting the position of the magnetic member 28 of the impeller 21. In the impeller position control section 4, a plurality of (typically three) electromagnets 41 and a plurality of (typically three) sensors 42 are respectively arranged at equiangular intervals such that the electromagnets 41 and the sensors 42 are spaced at equiangular intervals. The electromagnet 41 consists essentially of a core and a coil. Three electromagnets 41 are arranged in the embodiment. More than three electromagnets, for example, four electromagnets may be arranged. By adjusting the electromagnetic forces of the electromagnets 41 in accordance with the results of detection of the position sensors 42 to be described later, forces acting on the impeller in a center axis (z-axis) direction can be balanced and moments about x and y axes perpendicular to the center axis (z-axis) can be equal to each other.

The position sensor 42 detects the distance of the gap between tie electromagnet 41 and the magnetic number 28.

An output indicating the detection is fed back to a control part 63 for controlling electric current or a voltage to be applied to the coil of the electromagnet 41. When a radial force as by gravity acts on the impeller 21, the impeller 21 is held at the center of the housing 20 by virtue of restoring forces of a magnetic flux between the first permanent magnet 25 of the impeller 21 and the permanent magnet 33 of the rotor 31 and restoring forces of a magnetic flux between the electromagnet 41 and the second magnetic member 28. Instead of using the position sensor 42, it is possible to use a sensor having a computing circuit for detecting the position of the magnetic member 28 of the impeller 21 by means of a waveform of electric current flowing through the electromagnet 41.

The control device 6 will be described below with reference to FIG. 1.

The control device 6 has an impeller position control function, an impeller rotation torque control function, and the impeller-floating position control function for changing the impeller-floating position of the impeller 21 inside the housing 20 by using the impeller position control function.

More specifically, the control device 6 has a control system main body 61, a motor driver 62, and the impeller position control part 63.

The motor diver 62 outputs a current, to the motor 34, corresponding to a motor-driving current value or a number of rotations of the motor 34 transmitted (instructed) thereto from the control part 65 to rotate the motor 34.

To maintain the floating position of the impeller 21 instructed (issued) by the body 61, the impeller position control part 63 controls electric current and/or a voltage applied to three electromagnets 41. Signals indicating the result obtained by the detection made by the three position sensors 42 are transmitted to the impeller position control part 63. Upon receipt of the signals, the impeller position control part 63 controls electric current flowing through the three electromagnets 41 so that forces acting in the center axis (z-axis) direction of the impeller 21 are balanced with one another and moments about the x-axis and the y-axis perpendicular to the center axis (z-axis) can be equal to each other. It is possible to transmit the result obtained by the detection made by the three position sensors 42 to the body 61 so that the body 61 outputs voltages to individual the three electromagnets 41.

The body 61 includes a storing portion (ROM) 64 of the control part 65, a CPU (not shown), a display part 66, an input part 67, an alarm lamp 83 and a buzzer 82 serving as alarm means. The display part 66 includes a portion 71 for displaying a set motor-driving current value, a portion 72 for displaying the set number of rotations of the motor, a portion 76 for displaying a number of rotations of the impeller 21 and a portion 76b for displaying a motor-driving current. The body 61 includes the input mode selection part 68 and a part 69 for inputting set values related to the rotation of the motor. The part 69 for inputting set values related to the rotation of the motor includes the set motor-driving current value input portion 69a and the set motor number-of-rotations input portion 69b as shown in FIGS. 1 and 6.

The storing portion 64 of the control part 65 of the embodiment stores the upper limit of the motor-driving current and the upper limit of the number of rotations of the motor. The upper limit values may be stored in the ROM as analog voltages. The control part 65 issues an instruction of flashing the alarm lamp 83 on and off or ringing the buzzer 82 if the operator inputs a set motor-driving current value more than the stored upper limit value thereof from the set motor-driving current input portion 69a. This is to inform the operator that inputting the set motor-driving current value is unacceptable. Thus, the operator inputs a different current value. Similarly, the control part 65 issues an instruction of flashing the alarm lamp 83 on and off or ringing the buzzer 82 if the operator inputs a set number of rotations of the motor more than the stored upper limit value thereof from the set motor number-of-rotations input portion 69b. Tis is to inform the operator that inputting the set number of rotations is unacceptable. Thus, the operator inputs a different number of rotations. Owing to the function of the control part 5, it is possible to prevent the motor from rotating in a condition in which there is a fear of occurrence of the power swing The input part may be so constructed that instead of digital values, analog values such as a volume or the like can be inputted thereto.

In the above-described embodiment, the occurrence of the power swing is prevented by the input limiting method. Instead, the occurrence of the power swing may be prevented by limiting an output, as shown in FIG. 7.

Figure 7:
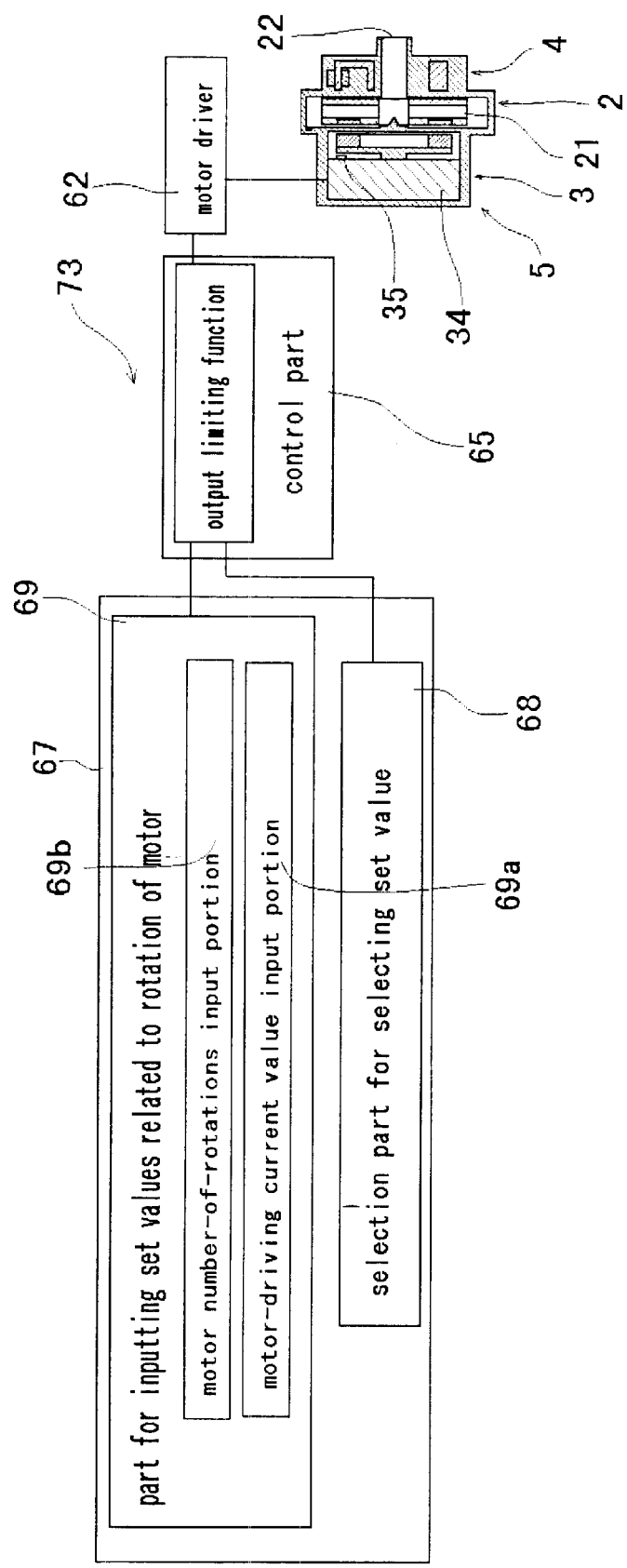
FIG. 7 is a block diagram showing another embodiment of the centrifugal fluid pump assembly of the invention.

In the output limiting method, a control device 73 of the pump assembly shown in FIG. 7 includes a motor-driving current value input portion 69a or the set motor number-of-rotations input portion 69b; and the motor rotation control part 65. The motor rotation control part 65 has a function of storing an upper limit value of the motor-driving current and a function of limiting a supply of the motor-driving current having a value more than the stored upper limit value to the motor. Because the motor rotation control device 65 has the above-described function, the motor can be prevented from being driven at a motor-driving current value more than the motor-driving current value at which there may be a danger of occurrence of the power swing. Thus, there is hardly a possibility of the occurrence of the power swing.

Using a liquid (for example, blood or liquid whose property is dose to blood, as described above) to be fed, a motor-driving current value at which the centrifugal pump has a power swing is examined. For safety, the power swing-causing current value thus detected or a value 20–50% lower than that is set as the upper limit value of the motor-driving Current value. The function of limiting the supply of the motor-driving current having a value more than the stored upper limit value to the motor includes a function of comparing the upper limit value thus stored with a motor-driving current value inputted at the motor-driving current input portion 69a or with a motor-driving current value computed from a number of rotations of the motor inputted at the set motor number-of-rotations input portion 69b and a motor rotation control function of controlling the rotation of the motor such that the motor rotates at an inputted motor-driving current value if the inputted motor-driving current value is less than the stored upper limit value thereof and of controlling the rotation of the motor such that the motor rotates at the stored upper limit value thereof if the inputted motor-driving current value is more than the stored upper limit value thereof.

In the output limiting method, the storing portion 64 of the control part 65 stores both the upper limit of the motor-driving current value and the upper limit of the number of rotations of the motor. Thus, if a set motor-driving current value inputted at the motor-driving current input portion 69a is more than the stored upper limit value, the control part 65 outputs the upper limit of the motor-driving current value and issues an instruction of flashing the alarm lamp 83 on and off and ringing the buzzer 82 to inform the operator that the set condition has been altered to the upper limit of the motor-driving current value. In this case, it is unnecessary for the operator to input a different current value. Similarly, if a set number of rotations of the motor inputted at the motor number-of-rotations input portion 69b is more than the stored upper limit, the control part 65 executes an output corresponding to the upper limit of the number of rotations of the motor anti issues an instruction of flashing the alarm lamp 83 on and off and ringing the buzzer 82 to inform the operator that the set condition has been altered to the upper limit of the number of rotations of the motor. In this case, it is also unnecessary for the operator to input a different current value.

Figure 8:
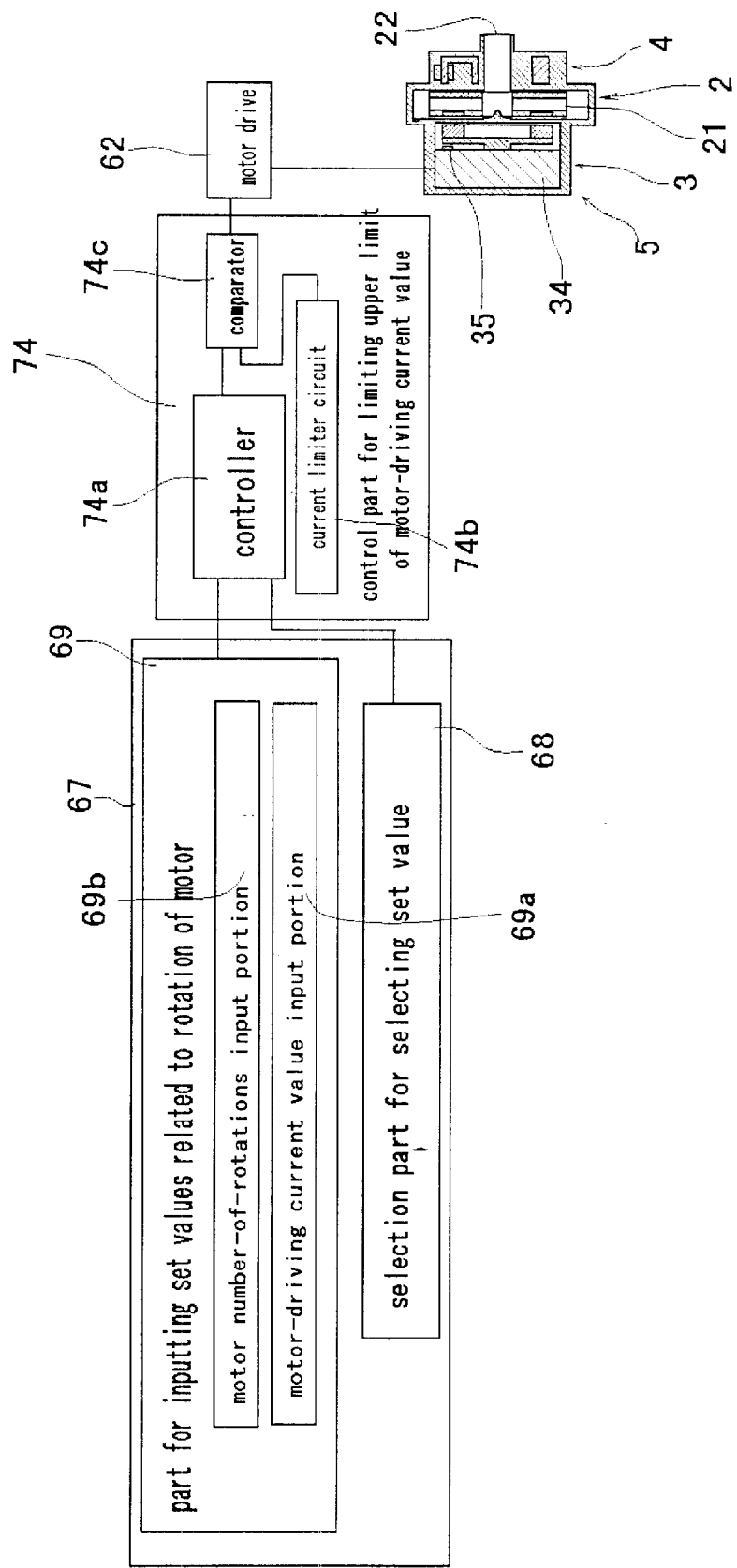
FIG. 8 is a block diagram showing still another embodiment of the centrifugal fluid pump assembly of the invention.

The comparing function of the control part 65 is performed by using the CPU (not shown) thereof or by using an electric circuit. When the comparing function is performed by using the electric circuit, as shown in the block diagram of FIG. 8, a control part (control part for controlling maximum value of motor-driving current value) 74 has a controller 74a, a current limiter circuit 74b, and a comparator 74c. The current limiter circuit 74b prevents electric current having a value more than the upper limit value of the motor-driving current value from being outputted to the motor. The comparator 74c compares the upper limit of the value of the motor-driving current outputted from the current limiter circuit 74b with a motor-driving current value outputted from the controller 74a or with a motor-driving current value computed from an inputted number of rotations of the motor, thus outputting the smaller current value to the motor driver 62.

As another example of the output limiting method, the control device may have an input portion for inputting a set number of rotations of the motor and a motor rotation control part. The control part has a function of storing the upper limit of the number of rotations of the motor, a comparing function of comparing the stored upper limit of the number of rotations of the motor with a set number of rotations of the motor inputted at the set motor number-of-rotations input portion, and a motor rotation control function of controlling the rotation of the motor such that the motor rotates at the set number of rotations of the motor if the set number of rotations of the motor is smaller than the stored upper limit of the number of rotations of the motor and controlling the rotation of the motor such that the motor rotates at the stored upper limit of the number of rotations of the motor if the set number of rotations of the motor is more than the stored upper limit value thereof.

Figure 9:
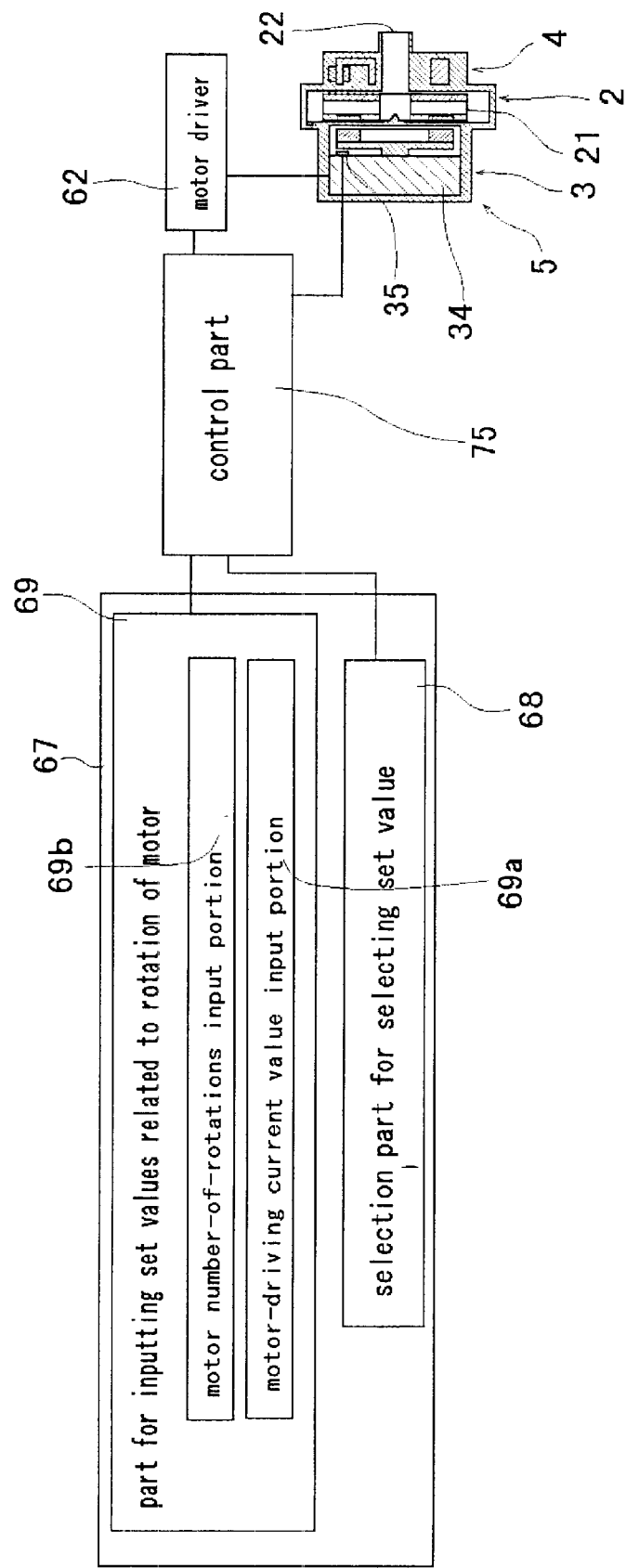
FIG. 9 is a block diagram showing still another embodiment of the centrifugal fluid pump assembly of the invention.

The control method to be carried out by the control part is not limited to the above-described input limiting method and output limiting method. For example, as shown in the block diagram of FIG. 9, the control method can be carried out by detecting the number of rotations of the rotor.

The control device of the embodiment has a motor rotation control part 75 electrically connected with a portion 35 for detecting the number of rotations of the motor. The motor rotation control part 75 has a function of storing the upper limit of the number of rotations of the motor and a control function of controlling the rotation of the motor such that a detected number of rotations of the motor does not exceed the upper limit of the number of rotations.

The impeller rotation torque generating section 3 has the sensor 35 for detecting the number of rotations of the motor 34 or that of the rotor 31. Upon receipt of a signal outputted from the sensor 35, the control part 75 computes the number of rotations of the motor 34 or that of the rotor 31. An optical or a magnetic sensor can be used as the sensor 35. The number of rotations of the motor 34 or that of the rotor 31 may be detected by a counter electromotive force that is generated in the motor coil.

The control part 75 has the function of storing the upper limit of the number of rotations of the motor and the comparing function of comparing the stored upper limit of the number of rotations of the motor with an actual (inputted) number of rotations of the motor. If the actual number of rotations of the motor is smaller than the upper limit of the number of rotations of the motor, the control part 75 does not execute a control. If the actual number of rotations of the motor is close to the upper limit of the number of rotations of the motor, the control part 75 adjusts a signal to be outputted to the motor driver so that the actual number of rotations of the motor does not exceed the upper limit of the number of rotations of the motor. This control method can also prevent the occurrence of the power swing.

An embodiment of the pump assembly of the invention shown in FIG. 10 will be described below.

Figure 10:
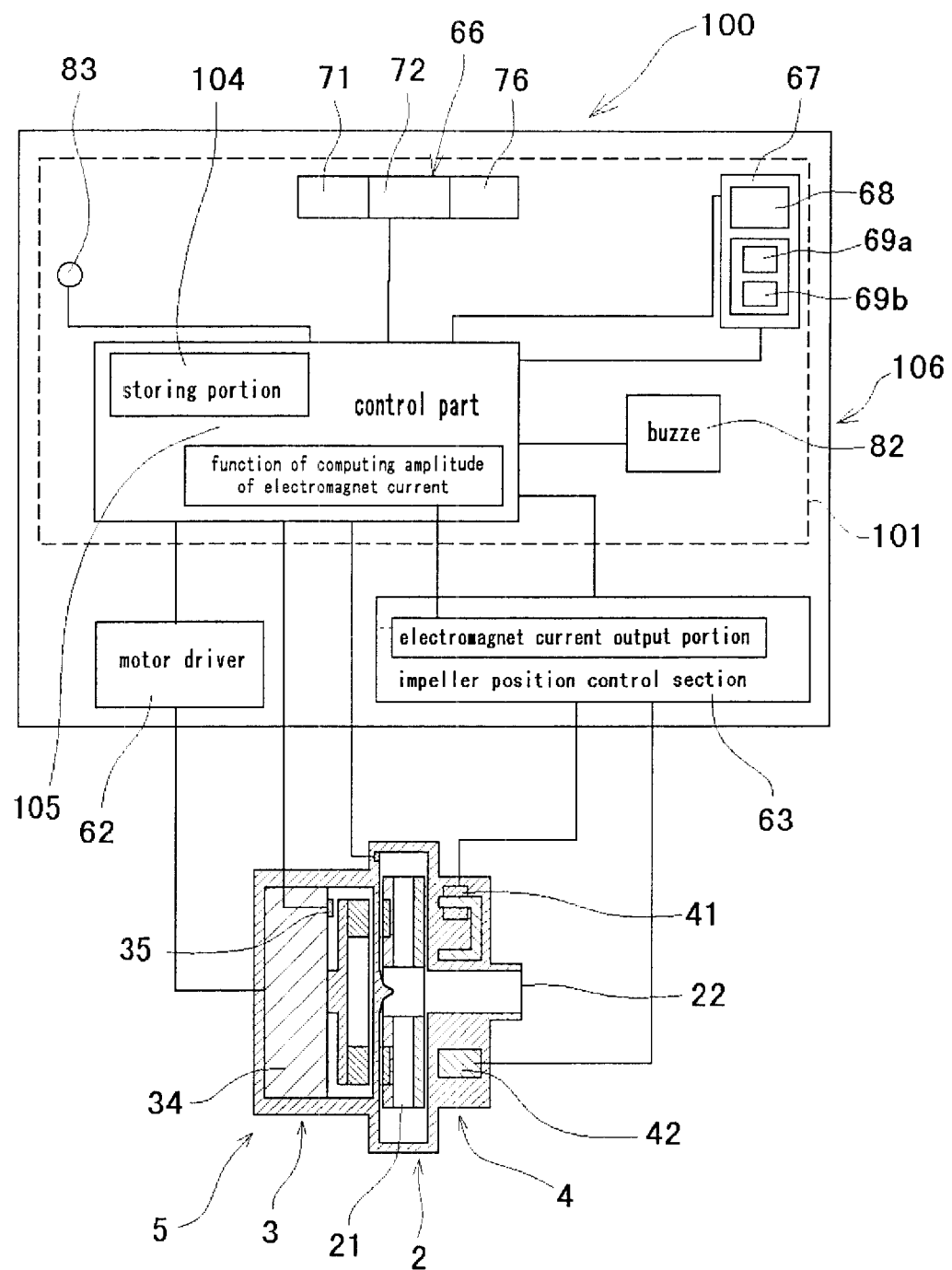
FIG. 10 is a block diagram showing still another embodiment of the centrifugal fluid pump assembly of the invention.
Figure 11:
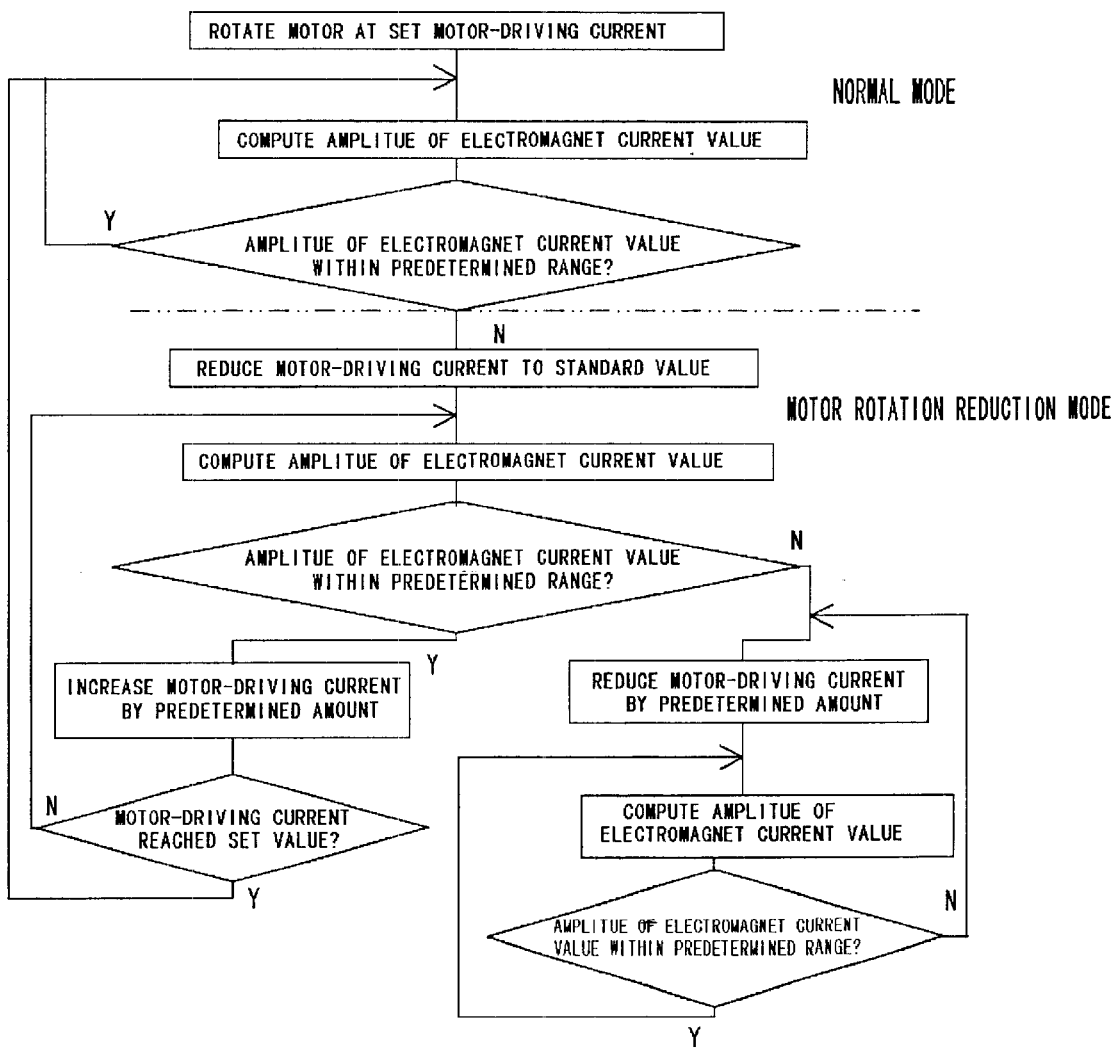
FIG. 11 is a flowchart for describing a control system of the embodiment of the centrifugal fluid pump assembly shown in FIG. 10.

FIG. 10 is a block diagram showing still another embodiment of the centrifugal fluid pump assembly of the invention. FIG. 11 is a flowchart for describing a control system of the embodiment of the pump assembly shown in FIG. 10.

When a load is increasingly applied to the rotating impeller, it shifts in its rotation direction in the magnet coupling between impeller and rotor. When the degree of the shift becomes excessive, the power swing (in other words, decoupling between impeller and rotor) occurs. There is no rotational center supported mechanically at the load-applied side in the pump assembly used in the invention. Therefore, a radial shift may occur between the impeller and the rotor due to eccentricity or whirling of the load-applied side. Tile power swing is caused if the eccentricity or whirling occurs in a high extent. The degree of the eccentricity or whirling is affected by molding accuracy of the impeller, presence of foreign matters such as thrombus formed in the chamber, and the like.

As a result of the present inventors energetic investigation, they have found that when a shift (eccentricity or whirling) occurs in a radial direction or in a rotational direction between the impeller and the rotor, the attracting force of the magnet coupling changes (more specifically, attractive force fluctuates or decreases) and that the change of the attractive force occurs due to variations in electric current flowing through the electromagnet of the impeller position control section. In particular, they have found that the variations in the electric current flowing through the electromagnet of the impeller position control section can be checked by computing an amplitude (difference between maximum current value and minimum current value) of the electric current flowing therethrough or by computing an average of the values of the electric currents flowing therethrough in a predetermined period of time.

A centrifugal fluid pump assembly 100 of the invention includes the centrifugal fluid pump 5 in which the impeller 21 rotates without contacting the housing 20 and a control device 106 for the centrifugal fluid pump 5.

The centrifugal fluid pump 5 includes the housing 20 having the blood inlet port 22 and the blood outlet port 23, the centrifugal fluid pump section 2 including the impeller 21 having the first magnetic material 25 and a second magnetic material 228 therein and rotating in the housing 20 to feed a fluid by a centrifugal force generated during its rotation, the impeller rotational torque generating section 3 including the rotor 31 having the magnet 33 for attracting the first magnetic material 25 of the impeller 21 and the motor 34 for rotating the rotor 31, and the impeller position control section 4 having the electromagnet 41 for attracting the second magnetic material 28 of the impeller 21.

The control device 106 has a monitoring function of monitoring electric current flowing through the electromagnet 41 and a motor control function of controlling the rotation of the motor such that the rotational speed of the motor is reduced when the amplitude (difference between the maximum current value and the minimum current value) of the electric current, flowing through the electromagnet, detected by the airrent monitoring function is more than a predetermined value.

The fundamental construction of the pump asseimnliy 100 is the same as that of the above-described pluiip assembly 1 shown in FIG. 1, except that the motor control function of the control device 106 of the pump assembly 100 is different from that of the control device 6 of the pump assembly 1.

To maintain the floating position of the impeller 21 instructed (issued) by the control device main body 61, the impeller position control part 63 of the control device 106 controls electric current and/or a voltage applied to three electromagnets 41. The control device 106 has the function of monitoring the electric current flowing thlough the electromagnet 41. A signal corresponding to a monitored current value is outputted from an electromagnet current value output portion to the control part 105. Based on the signal corresponding to the value of the current flowing through the electromagnet 41, the control part 105 computes the amplitude (difference between maximum current value and minimum current value) of the electric current flowing therethrough. Because three electromagnets 41 are provided in the embodiment, the amplitude of the electric current flowing therethrough is the average of the amplitudes of the electric currents flowing through the three electromagnets. A pemissible maximum amplitude (predetemiined amplitude) of the electric current flowing therethrough is stored in the storing portion 104 of the control part 105. The control part 105 has a ,fmction of comparing the permissible predetermiined amplitude of the electric current flowing through the electromagnet 41 and a computed amplitude of the electric current flowing therethrough with each other. Thus, if the computed amplitude of the electric current flowing therethrough is more than the predetermined amplitude, the control part 105 controls the rotation of the motor such that the rotational speed of the motor is reduced by outputting an instruction signal to the motor driver 62. The pemussitle maximum amplitude (predetermined amplitude) of the electric current flowing through the electromagnet 41 is 1.0–1.4A, although it depends on the size of the pump.

The control operation is described below with reference to the flowchart of FIG. 11.

The motor 34 rotates at a set motor-driving current value inputted at the motor-drivilg current input portion 69a. During the rotation of the motor 34, the control part always computes the amplitude of the electric current flowing through the electromagnet and determine every predetermined period of time whether the amplitude of the electric cuiient flowing theretluough falls within a predetermined range (upper limit: pemissible maximum amplitude of electric current flowing therethrough). If YES (within a predetermined range or under the permissible maximiun amplitude of electric current), the control part repeatedly returns to the step at which it computes the amplitude of the electric current flowing therethrough. If it is determined that the amplitude of the electric current flowing therethrough is out of the predetemiined range (for example, if electric current flowing therethrough exceeds permissible maximum amplitude), the control part goes to a motor rotation reduction mode in which the control part reduces the motor-driving current to a standard value [current value lower by some extent than set current value inputted at motor-driving current input portion, preferably, 70–80% of set current value or preset standard value (0.3–1.0A)] or the control part reduces the number of rotations of the motor to 1600–2000 rpm. Thereafter, the control part computes the amplitude of the electric current flowing therethrough and every predetermined period of time, determines whether the amplitude of the electric current flowing therethrough falls within the predetermined range (upper limit: permissible maximiun amplitude) if YES (within a predetermined range or under the permissible maximum amplitude of electric current), the control part goes to a step at which it increases the motor-driving current value by the predetermined amount (amount smaller than reduction amount at initial time, preferably, 5–10% of set current value or 0.05–0.1A) or increases the number of rotations of the motor by 50–100 rpm. Then, the control part determines whether the increased motor-driving current value has reached the set motor-driving current value (value initially set). If NO, the control part computes the amplitude of the electric current flowing through the electromagnet again and determines whether the amplitude of the electric current flowing therethrough falls within the predetermined range. It YES (within a predetermined range or under the permissible maximiun amplitude of electric current), the control part returns to the step at which it increases the motor-driving current by the predetermined amount (amount smaller than the reduction amount at initial time, preferably, 5–10% of set current value or 0.05–0.1A) or increases the number of rotations of the motor by 50–100 rpm. That is, in this control method, after the current value or the number of rotations of the motor is reduced by some extent, the current value or the number of rotations of the motor is increased stepwise. If it is determined that the amplitude of the electric current flowing therethrough is out of the predetermined range in the step of increasing the current value or the number of rotations of the motor, the motor-driving current value is reduced by a predetermined value (lower than reduction amount at initial time). Then, the control part computes the amplitude of the electric current flowing through the electromagnet again and determines whether the amplitude of the electric current flowing therethrough falls within the predetermined range. If it is determined that the amplitude of the electric current flowing therethrough is out of the predetermined range, the motor-driving current value is further reduced by the predetermined value. The reduction of the current value is repeated until the amplitude of the electric current flowing therethrough becomes within the predetermined range. The reduced current value is maintained until the amplitude of the electric current flowing therethrough becomes out of the predetermined range again. If the amplitude of the electric current flowing therethrough becomes out of the predetermined range, the motor-driving current value is reduced until the amplitude of the electric current flowing therethrough becomes within the predetermined range.

The execution of such a control prevents the occurrence of the power swing, allows the motor to be rotated at the maximum current value in the range in which the occurrence of the can be avoided, a flow rate to be secured in some extent, and prevents a back flow of the liquid in the pump. Further, in the control, when the motor-driving current has reached the set motor-driving current value as a result of repeatedly increasing it by the predetermined value the control part can return to the normal mode.

When the control part 105 moves to the motor rotation reduction mode, the alarm lamp 83 flashes on and off or the buzzer 82 rings to inform the transition of the mode. When the control part has returned to the normal mode from the motor rotation reduction mode, the operation of the alarm lamp 82 or the buzzer 82 is stopped.

An embodiment of the pump assembly of the invention shown in FIG. 12 will be described below.

Figure 12:
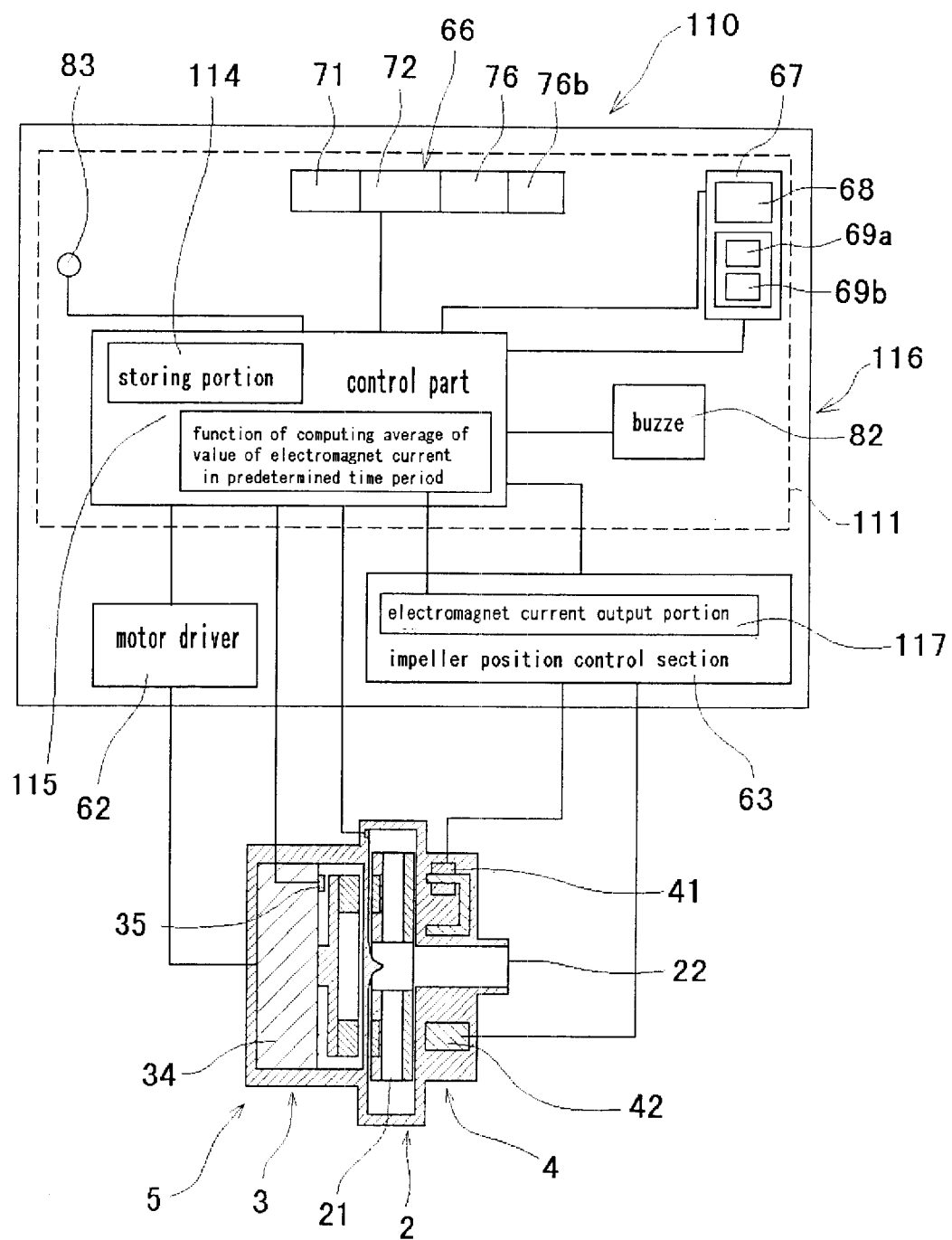
FIG. 12 is a block diagram showing still another embodiment of the centrifugal fluid pump assembly of the invention.
Figure 13:
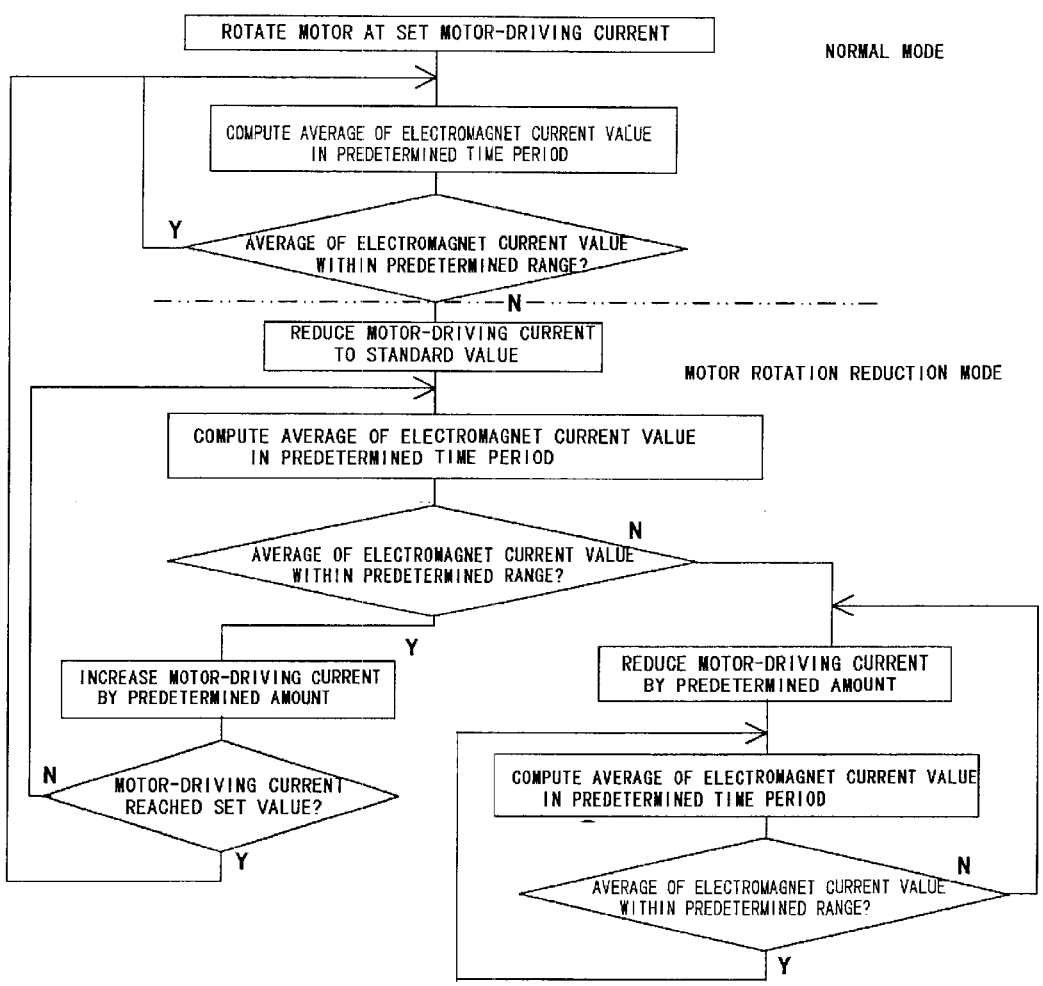
FIG. 13 is a flowchart for describing a control system of the embodiment of the centrifugal fluid pump assembly shown in FIG. 12.

FIG. 12 is a block diagram showing still another embodiment of the centrifugal fluid pump assembly of the invention. FIG. 13 is a flowchart for describing a control system of the pump assembly shown in FIG. 12.

A centrifugal fluid pump assembly 110 of the invention includes the centrifugal fluid pump 5 in which the impeller 21 rotates without contacting the housing 20 and a control device 116 for the centrifugal fluid pump 5.

The centrifugal fluid pump 5 includes the housing 20 having the blood inlet port 22 and the blood outlet port 23, the centrifugal fluid pump section 2 inducing the impeller 21 having the first magnetic material 25 and a second magnetic material 28 therein and rotating in the housing 20 to feed a fluid by a centrifugal force generated during its rotation, the impeller rotational torque generating section 3 including the rotor 31 having the magnet 33 for attracting the first magnetic material 25 of the impeller 21 and the motor 34 for rotating the rotor 31, and the impeller position control section 4 having the electromagnet 41 or attracting the second magnetic material 28 of the impeller 21.

The control device 116 has a current monitoring function of monitoring an average of values of electric currents flowing through the electromagnet 41 in a predetermined period of time and a motor control function of controlling the rotation of the motor such that the rotational speed of the motor decreases when the average of values of electric currents becomes less than a predetermined value.

The fundamental constriction of the pump assembly 110 is the same as that of the above-described pump assembly 1 shown in FIG. 1 except that the motor control function of the control device 116 of the pump assembly 110 is different from that of the control device 6 of the pump assembly 1. In the motor control to be made by the control device of the pump assembly shown in FIGS. 10 and 11, the transition to the motor control is executed based on the amplitude of the electric current flowing through the electromagnet, whereas in the motor control to be made by the control device 116 of the pump assembly 110, the transition to the motor control is executed based on the average of values of electric currents flowing therethrough.

To maintain the floating position of the impeller 21 instructed (issued) by the control device main body 111, the impeller position control part 63 of the control device 116 controls electric current and/or a voltage applied to three electromagnets 41. The control device 116 has the function of monitoring the electric current flowing through the electromagnet 41. A signal corresponding to a monitored current value is outputted from an electromagnet current value output portion 117 to the control part 115. Based on the signal corresponding to the monitored current value, the control part 115 computes an average of values of electric currents flowing therethrough in a predetermined period of time (for example, 0.2–5.0 seconds.) Because the impeller position control section 4 has three electromagnets 41 in the embodiment, the control part 115 computes the average for three averages of values of electric currents flowing through each of the three electromagnets 41. The storing portion 114 of the control part 115 stores an average (predetermined average value) of permissible minimum values of the electric current flowing through the electromagnet 41 or values related to a permissible minimum value of the electric current flowing therethrough, namely, an integrated minimum value of the electric current flowing therethrough. The control part 115 has the function of comparing a computed average (or integrated value) of values of the electric currents flowing therethrough with the predetermined average value. If the computed average (or integrated value) of values of the electric currents flowing therethrough is more than the predetermined average value, the control part 105 controls the rotation of the motor such that the rotational speed of the motor is reduced by outputting any instruction signal to the motor driver. The average (predetermined average value) of permissible minimum values of the electric currents flowing through the electromagnet 41 is 0.7–1.0A, although it depends on the size of the pump.

The control operation of the control device 116 of the pump assembly 110 of this embodiment is described below with reference to the flowchart of FIG. 13.

The motor 34 rotates at a set motor-driving current value inputted at the motor-driving current input portion 69a. During the rotation of the motor 34, the control part 115 always computes the average of the values of the electric current flowing through the electromagnet 114 while the control part determines every predetermined period of time whether the average of the values of the electric currents flowing through the electromagnet falls within a predetermined range [upper limit: 2–3A, lower limit: average (integrated value) of permissible minimum values of the electric currents flowing through the electromagnet]. If YES (within a predetermined range), the control part repeatedly returns to the step at which the control part computes the average (integrated value) of the values of the electric current flowing therethrough. If it is determined that the average (integrated value) of the values of the electric current flowing therethrough is out of the predetermined range [for example, if average of values of electric current flowing therethrough is smaller than average (integrated value) of permissible minimum values of electric currents flowing therethrough], the control part 115 goes to a motor rotation reduction mode in which the control part 115 reduces the motor-driving current value to a set value (value lower by some extent than standard current value inputted at motor-driving current input portion 69a, preferably, 70–80% of set current value). Thereafter, the control part computes the average (integrated value) of the values of the electric currents flowing therethrough and determines every predetermined period of time whether the average (integrated value) of the values of the electric currents flowing there through falls within the predetermined range [upper limit: 2–3A, lower limit: average (integrated value) of permissible minimum values of electric currents flowing therethrough]. If YES (within a predetermined range), the control part increases the motor-driving current value by a predetermined amount (amount smaller than reduction amount at previous time, preferably, 70–80% or 5–10% of set current value). Then, the control part 115 determines whether the increased motor-driving current has reached the set motor-driving current value (initial set value). If NO, the control part computes the average of the values of the electric currents flowing therethrough again and determines whether the average of the values of the electric currents flowing therethrough falls within the predetermined range. If YES, the control part 115 increases the motor-driving current by the predetermined amount (amount smaller than reduction amount at previous time) repeatedly. That is, in this control method, after the current value is reduced by some extent, the current value is increased stepwise. If it is determined that the average of the values of the electric currents flowing therethrough is out of the predetermiined range in the process of increasing the current value, the control part 115 reduces the motor-driving current value by the predetermined amount (amount smaller than reduction amount at the initial time, preferably, 70–80% of set current value or 5–10% of reduction amount of electric current at previous time). Then, the control part 115 computes the average of the values of the electric currents flowing therethrough again and determines whether the average of the values of the electric currents flowing therethrough falls within the predetermined range. If it is determined that the average of the values of the electric currents flowing therethrough is out of the predetermined range, the control part 115 further reduces the motor-driving current by the predetermined amount. The reduction of the current value is repeated until the average of the values of the electric currents flowing therethrough becomes within the predetermined range. The reduced current value is maintained until the average of the values of the electric currents flowing therethrough becomes out of the predetermined range again. If it is determined that the average of the values of the electric currents flowing therethrough has become out of the predetermined range again, the control part 115 reduces the motor-driving current value until the average of the values of the electric currents flowing therethrough becomes within the predetermined range.

The execution of such a control prevents the occurrence of the power swing and allows the motor to be rotated at the maximum current value in the level in which the occurrence of the can be avoided, and a flow rate to be secured in some extent. In the control, when the motor-driving current has reached the set motor-driving current value as a result of repeatedly increasing the motor-driving current value by the predetermined value, the control part can return to the normal mode from the motor rotation reduction mode.

When the control part 115 has returned to the normal mode from the motor rotation reduction mode, the operation of the alarm lamp 82 or the buzzer 82 is stopped.

Figure 14:
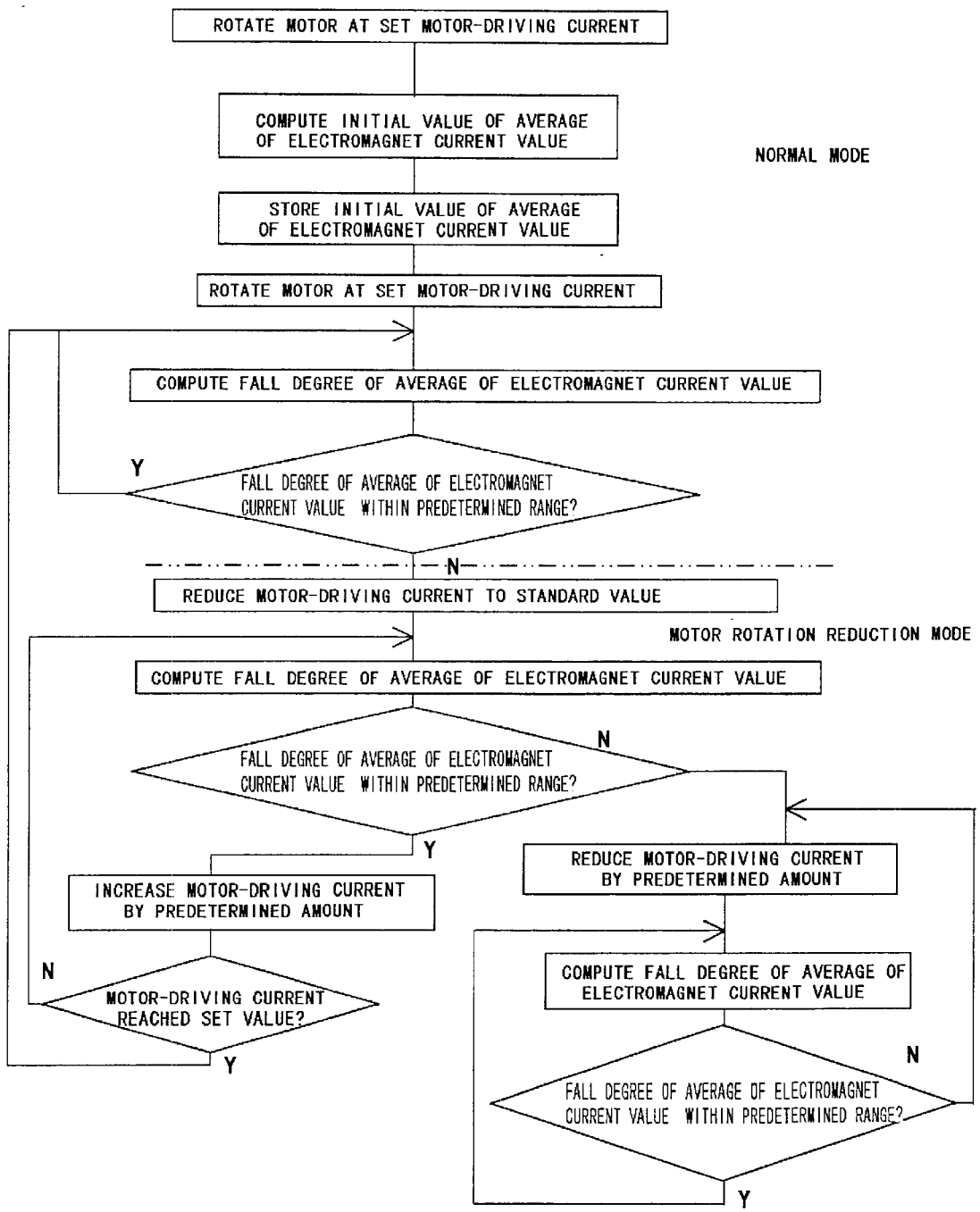
FIG. 14 is a flowchart for describing a control system of still another embodiment of the centrifugal fluid pump assembly of the invention.

In addition to the above-described control to be made by directly using the average of the values of the electric currents flowing therethrough, it is possible to control the motor by using a fall degree of the average of the values of the electric currents flowing therethrough relative to the average of the values of the electric currents flowing therethrough in an early period of time after the actuation of the centrifugal pump. In this case, the control part has a function of computing the average of the values of the electric currents flowing therethrough in the early period of time after the actuation of the centrifugal pump, a function of storing a computed result, a function of continuously computing the average of the values of the electric currents flowing therethrough, and a function of computing the fall degree (1-current time average of values of electric currents flowing therethrough/average of values of electric currents flowing therethrough in early period of time after the actuation of centrifugal pump) of the average of the values of the electric currents flowing therethrough by using the average of values of initial-time electric currents flowing therethrough and a current-time average of the values of the electric currents flowing therethrough. when the fall degree of the average exceeds a predetermined range (namely, fall degree of average of permissible maximum values of electric currents flowing therethrough or pemissible maximum fall degree of average of electric currents flowing through electromagnet), the control part controls the rotation of the motor such that the rotational speed of the motor is reduced by outputting an instruction signal to the motor driver. The fall degree (current-time average of values of electric currents flowing through electromagnet/current value when centrifugal pump floats and does not rotate) of average of permissible maximum values of electric currents flowing therethrough is preferably 60–80%. The flow in this control is shown in FIG. 14.

With reference to the flowchart of FIG. 14, an embodiment of the control is described below.

The motor 34 starts to rotate at a set motor-driving current value inputted at the motor-driving current input portion 69a. The control part computes the average of the values of the electric currents flowing through the electromagnet immediately or a predetermined period of time elapses after the motor starts to rotate, and an initial value is stored in the storing portion of the control part. During the rotation of the motor 34, the control part always computes the average of the values of the electric currents flowing therethrough and compares the average of the values thereof and an initial value of the average with each other to compute the fall degree (1-current-time average of values of electric currents flowing therethrough/average of values of electric currents flowing therethrough in early period of time after actuation of centrifugal pump) of the average of the values of the electric currents flowing therethrough. It is determined every predetermined period of time whether the average of the values of the electric currents flowing therethrough falls within a predetermined range (smaller than the permissible maximum fall degree of average of electric currents flowing through electromagnet). If YES (within a predetermined range), the control part repeatedly returns to the step at which it computes the fall degree of the average of the values of the electric currents flowing therethrough. If it is determined that the fall degree of the average of the values of the electric currents flowing therethrough is out of the predetermined range (more than the permissible maximum fall degree of average of electric currents flowing through electromagnet), the control part goes to a motor rotation reduction mode in which the control part 115 reduces the motor-driving current to the set value (value lower by some extent than value inputted at motor-driving current input portion 69a, preferably, 70–80% of set current value). Thereafter, the control part computes the fall degree of the average of the values of the electric currents flowing therethrough and determines every predetermined period of time whether the fall degree of the average of the values of the electric currents flowing therethrough falls within the predetermined range (whether the fall degree of the average thereof does not exceed the permissible maximum fall degree of average of electric currents flowing through electromagnet). If YES (within a predetermined range), the control part increases the motor-driving current by a predetermined amount (amount smaller than reduction amount at previous time, preferably, 70–80% of set current value or 5–10% of reduction amount of electric current at previous time). Then, the control part determines whether the increased motor-driving current has reached the set motor-driving current value (initial set value). If NO, the control part computes the fall degree of the average of the values of the electric currents flowing therethrough again and determines whether the fall degree of the average of the values of the electric currents flowing therethrough falls within the predetermined range. If YES (within a predetermined range), the control part increases the motor-driving current by the predetermined amount (amount smaller than reduction amount at previous time, preferably, 70–80% of set current value or 5–10% of reduction amount of electric current at previous time) repeatedly. That is, in this control method, after the current value is reduced by some extent, the current value is increased stepwise. If it is determined that the fall degree of the values of the electric currents flowing therethrough is out of the predetermined range (more than the permissible maximum fall degree of average of electric currents flowing through electromagnet) in the process of increasing the current value, the motor-driving current is reduced by the predetermined amount (amount smaller than reduction amount at initial time, preferably, 70–80% of set current value or 5–10% of reduction amount of current value at previous time). Then, the control part computes the fall degree of the average of the values of the electric currents flowing therethrough again and determines whether the fall degree of the average of the values of the electric currents flowing therethrough falls within the predetermined range. If it is determined that the fall degree of the average of the values of the electric currents flowing therethrough is out of the predetermined range, the control part further reduces the motor-driving current value by the predetermined value. The reduction of the current value is repeated until the fall degree of the average of the values of the electric currents flowing therethrough becomes within the predetermined range. The reduced current value is maintained until the fall degree of the average of the values of the electric currents flowing therethrough becomes out of the predetermined range again. If it is determined that the fall degree of the average of the values of the electric currents flowing therethrough has become out of the predetermined range again, the control part reduces the motor-driving current until the fall degree of the average of the values of the electric currents flowing therethrough becomes within the predetermined range.

The execution of such a control prevents the occurrence of the power swing and allows the motor to be rotated at the maximum current value in the level in which the occurrence of the can be avoided and a flow rate to be secured in an appropriate degree. In the control, when the motor-driving current has reached the set value as a result of repeatedly increasing the motor-driving current by the predetermined value, the control part can return to the normal mode from the motor rotation reduction mode.

When the control part 115 has returned to the normal mode from the motor rotation reduction mode, the operation of the alarm lamp 82 or the buzzer 82 is stopped.

The centrifugal fluid pump assembly of the invention comprises the centrifugal fluid pimp and the control device for the centrifugal fluid pump.

The control device has the input portion for inputting a set number of rotations of the motor or the input portion for inputting a set motor-driving current value; and the function of limiting an input of a number of rotations of the motor more than the predetermined number of rotations or limiting an input of the motor-driving current having a value more than the predetermined value. In this construction, the motor does not rotate at a number of rotations more than the predetermined number of rotations. Thus, it is possible to prevent the power swing from occurring between the impeller and the rotor.

The control device has the input portion for inputting a set motor-driving current value or the input portion for inputting a set number of rotations of the motor, and the motor rotation control part. The motor rotation control part has the function of storing the upper limit value of the motor-driving current and the function of limiting the input of the set motor-driving current having a value more than the stored upper limit value thereof In this construction, the motor does not rotate at a current value more than the upper limit of the motor-driving current. Thus, it is possible to prevent the power swing from occurring between the impeller and the rotor.

The control device has the input portion for inputting a set number of rotations of the motor and the motor rotation control part. The control part has the function of storing the upper limit of the number of rotations of the motor; the comparing function of comparing the stored upper limit of the number of rotations of the motor with a set number of rotations of the motor inputted at the input portion; and the motor rotation control function of controlling the rotation of the motor such that the motor rotates at the set number of rotations of the motor, if the set number of rotations of the motor is smaller than the upper limit of the number of rotations of the motor and such that the motor rotates at the upper limit of the number of rotations of the motor if the set number of rotations of the motor is more than the upper limit value thereof. In this construction, the motor does not rotate at a number of rotations more than the upper limit of the number of rotations of the motor. Thus, it is possible to prevent the power saving from occurring between the impeller and the rotor.

The motor rotation control part has the function of storing the upper limit of number of rotations of the motor and the control function of controlling the rotation of the motor such that a detected number of rotations of the motor does not exceed the upper limit of the number of rotations. In this construction, the motor does not rotate at a number of rotations more than the upper limit of the number of rotations of the motor. Thus, it is possible to prevent the power swing from occurring between the impeller and the rotor.

The control device has the monitoring function of monitoring electric current flowing through the electromagnet; and the motor control function of controlling the rotation of the motor such that the rotational speed of the motor is reduced when the amplitude of electric current, flowing through the electromagnet, detected by the current monitoring function is more than the predetermined value. In this construction, it is possible to prevent the power swing from occurring between the impeller and the rotor.

The control device has the monitoring function of monitoring electric current flowing through the electromagnet; and tie motor control function of controlling the rotation of the motor such that the rotational speed of the motor is reduced when an average of values of the electric currents, detected by the monitoring function, flowing through the electromagnet in a predetermined period of time is less than the predetermined value. In this construction, it is possible to prevent the power swing from occurring between the impeller and the rotor.

The control device has the monitoring function of monitoring electric current flowing through the electromagnet; and the motor control function of controlling the rotation of the motor such that the rotational speed of the motor is reduced when the fall degree of the average of the values of the electric currents flowing therethrough relative to the average of values of the electric currents flowing therethrough in an early period of time after an actuation of the pump assembly exceeds a predetermined range. In this construction, it is possible to prevent the power swing from occurring between the impeller and the rotor.

An embodiment of the pump assembly of the invention applied to a blood pump will be described below.

A centrifugal fluid pump assembly 200 of the invention includes a centrifugal fluid pump 205 in which an impeller 221 rotates without contacting the housing 220; and a control device 206 for the centrifugal fluid pump 205.

The centrifugal fluid pump 205 includes a housing 220 having a blood inlet port 222 and a blood outlet port 223, a centrifugal fluid pump section 202 including an impeller 221 having a first magnetic material (permanent magnet) 225 and a second magnetic material 228 disposed therein and rotating in the housing 220 to feed a fluid by a centrifugal force generated during its rotation, an impeller rotational torque generating section 203 including a rotor 231 having a magnet 233 for attracting the first magnetic material 225 of the impeller 221 and a motor 234 for rotating the rotor 231, an impeller position control section 204 having an electromagnet 241 for attracting the impeller 221 (more specifically, for attracting the magnetic member 228 of the impeller 221) thereto, and a position sensor 242 (position sensor for detecting position of magnetic member of impeller).

The control device 206 has a monitoring function of monitoring electric current flowing through the electromagnet; a monitoring function of monitoring motor-driving current; a monitoring function of monitoring the number of rotations of the motor; and a function of determining whether or not the impeller has a power swing (in other words, a function of determining whether or not a decoupling occurs between the impeller and the rotor) by utilizing a current value monitored by the monitoring function of monitoring the electric current flowing through the electromagnet, a value of the motor-driving current monitored by the monitoring function of monitoring the motor-driving current, and the number of rotations of the motor monitored by the monitoring function of monitoring the number of rotations thereof.

As shown in FIGS. 16 through 19, the centrifugal fluid pump 205 of the centrifugal fluid pump assembly includes a housing 220 having the blood inlet port 222 and the blood outlet port 223, the centrifugal fluid pump section 202 including the impeller 221 rotating inside the housing 220 to feed blood by the centrifugal force generated during its rotation, the impeller rotation torque generating section 203 (uncontrolled magnetic bearing section) for the impeller 221, and the impeller position control section 204 (controlled magnetic bearing section) for the impeller 221.

The uncontrolled magnetic bearing section 203 and the controlled magnetic bearing section 204 cooperate such that the impeller 221 rotates while it is held in position within the housing 220.

The housing 220 has the blood inlet port 222 and the blood outlet port 223 and is formed of a non-magnetic material. The housing 220 defines therein the blood chamber 224 in fluid communication with the blood inlet and outlet ports 222 and 223. The impeller 221 is accommodated inside the housing 220. The blood inlet port 222 protrudes from near the center of the upper surface of the housing 220 in a substantially vertical direction. The blood outlet port 223 projects from a side surface of the generally cylindrical housing 220 in a tangential direction.

The disc-shaped impeller 221 having a through-hole in the center thereof is accommodated within the blood chamber 224 of the housing 220. The impeller 221 includes a disc-shaped member or a lower shroud 227 defining the lower surface thereof, an annular plate-shaped member or an upper shroud 228 defining the upper surface thereof and opening at the center thereof, and a plurality of (six in the embodiment) vanes 218 formed between the lower and upper shroud 227 and 228. The vanes 218 define a corresponding plurality of (six in the embodiment) blood passages 226 between two adjacent ones and between the lower and upper shrouds. Each blood passage 226 extends from the center opening to the outer periphery of the impeller 221 in a curved fashion. Differently stated, the vanes 218 are formed between adjacent blood passages 226. In the embodiment, the vanes 218 and blood passages 226 are respectively provided at equiangular intervals and in substantially the same shape.

A plurality of magnetic materials 225 (six in the embodiment) are embedded in the impeller 221. The magnetic materials 225 are permanent magnets and serve as follower magnets. The magnetic materials 225 are provided in the impeller 221 so that the impeller 221 is attracted away from the blood inlet port 222 by a permanent magnet 233 provided in the rotor 231 of the rotational torque generating section 203 to be described later and that the rotational torque is transmitted from the torque generating section 203 to the impeller 221. Such plural discrete magnetic materials 225 embedded in the impeller 221 ensure magnetic coupling with the rotor 231 to be described later can be ensured. Each magnetic material 225 (permanent magnet) is preferably circular in a horizontal cross section. Instead, it is possible to use a ring-shaped magnet having multi-poles (for example, 24 poles). In other words, a plurality of small magnets may be arranged in the shape of a ring such that positive and negative poles alternate with each other.

The impeller 221 further includes a magnetic member 228 which itself constitutes an upper shroud or which is attached to the upper shroud. In the embodiment, the upper shroud in its entirety is constructed of the magnetic member 228. The magnetic member 228 is provided so that an electromagnet 241 of the impeller position control section 204 to be described later magnetically attracts the impeller 221 toward the blood inlet port 222. The magnetic member 228 may be formed of magnetic stainless steel, nickel or soft iron.

The impeller position control section 204 and the rotational torque generating section 203 constitute a non-contact type magnetic bearing, which magnetically attracts the impeller 221 front opposite directions to steadily hold the impeller 221 at a proper position out of contact with the neuter surface of the housing 220 so that the impeller 221 may rotate within the housing 220 without contacting its inner surface.

Included in the rotational torque generating section 203 are the housing 220, the rotor 231 accommodated in the housing 220, and a motor 234 (whose internal structure is not shown) for rotating the rotor 231. The rotor 231 includes a rotating disc 232 and a plurality of permanent magnets 233 disposed on one surface (facing the fluid pump) of the rotating disc 232. The rotor 231 at its center is fixedly secured to the rotating shaft of the motor 234. A plurality of the permanent magnets 233 are equiangularly distributed in accordance with the arrangement mode of the permanent magnets 225 of the impeller 221. That is, the number and location of permanent magnets 233 are coincident with the number and location of the permanent magnets 225.

The impeller rotation torque generating section 203 is not limited to the illustrated one having the rotor and motor. For example, a plurality of stator coils may be used as long as it can attract the permanent magnets 225 of the impeller 221 and achieve the impeller 221 for rotation.

Included in the impeller position control section 204 are a plurality of electromagnets 241 accommodated in the housing 220 and attracting the magnetic number 228 of the impeller 221 thereto and a plurality of position sensors 242 for detecting the position of the magnetic member 228 of the impeller 221. In the impeller position control section 204, a plurality of (typically three) electromagnets 241 and a plurality of (typically three) sensors 242 are respectively arranged at equiangular intervals such that the electromagnets 241 and the sensors 242 are spaced at equiangular intervals. The electromagnet 241 consists essentially of a core and a coil. Three electromagnets 241 are arranged in the embodiment. More than three electromagnets, for example, four electromagnets may be arranged. By adjusting the electromagnetic forces of the electromagnets 241 in accordance with the results of detection of the position sensors 242 to be described later, forces acting on the impeller in a center axis (z-axis) direction can be balanced and moments about x and y axes perpendicular to the center axis (z-axis) can be equal to each other.

The position sensor 242 detects the distance of the gap between the electromagnet 241 and the magnetic member 228. An output indicating the detection is fed back to a control part 256 for controlling electric current or a voltage to be applied to the coil of the electromagnet 241. when a radial force as by gravity acts on the impeller 221, the impeller 221 is held at the center of the housing 220 by virtue of restoring forces of a magnetic flux between the permanent magnet 225 of the impeller 221 and the permanent magnet 233 of the rotor 31 and restoring forces of a magnetic flux between the electromagnet 241 and the magnetic member 228. Instead of using the position sensor 242, it is possible to use a sensor having a computing circuit for detecting the position of the magnetic member 228 of the impeller 221, based on a waveform of electric airrent flowing through the electromagnet 241.

Figure 15:
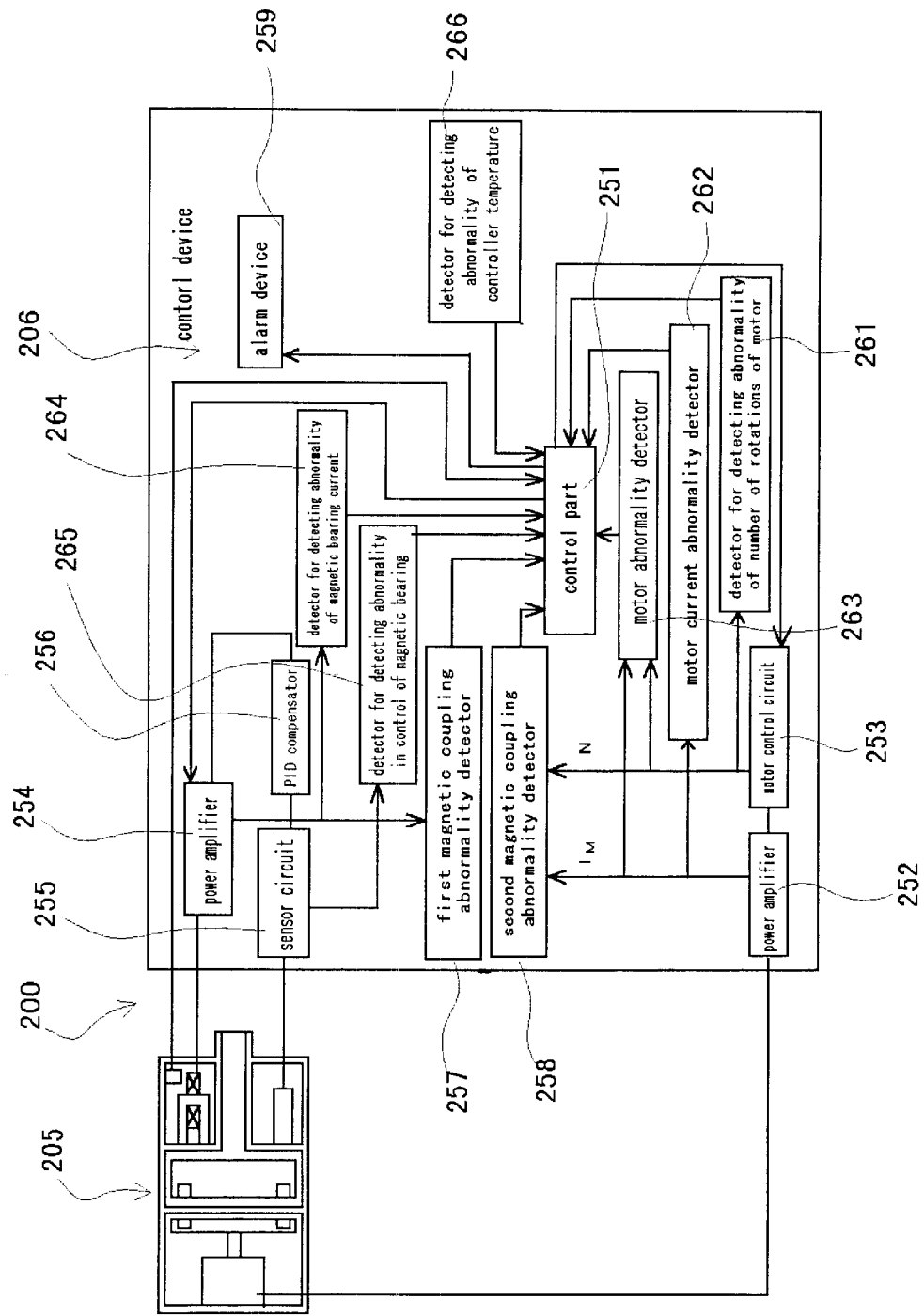
FIG. 15 is a block diagram showing still another embodiment of the centrifugal fluid pump assembly of the invention.
Figure 16:
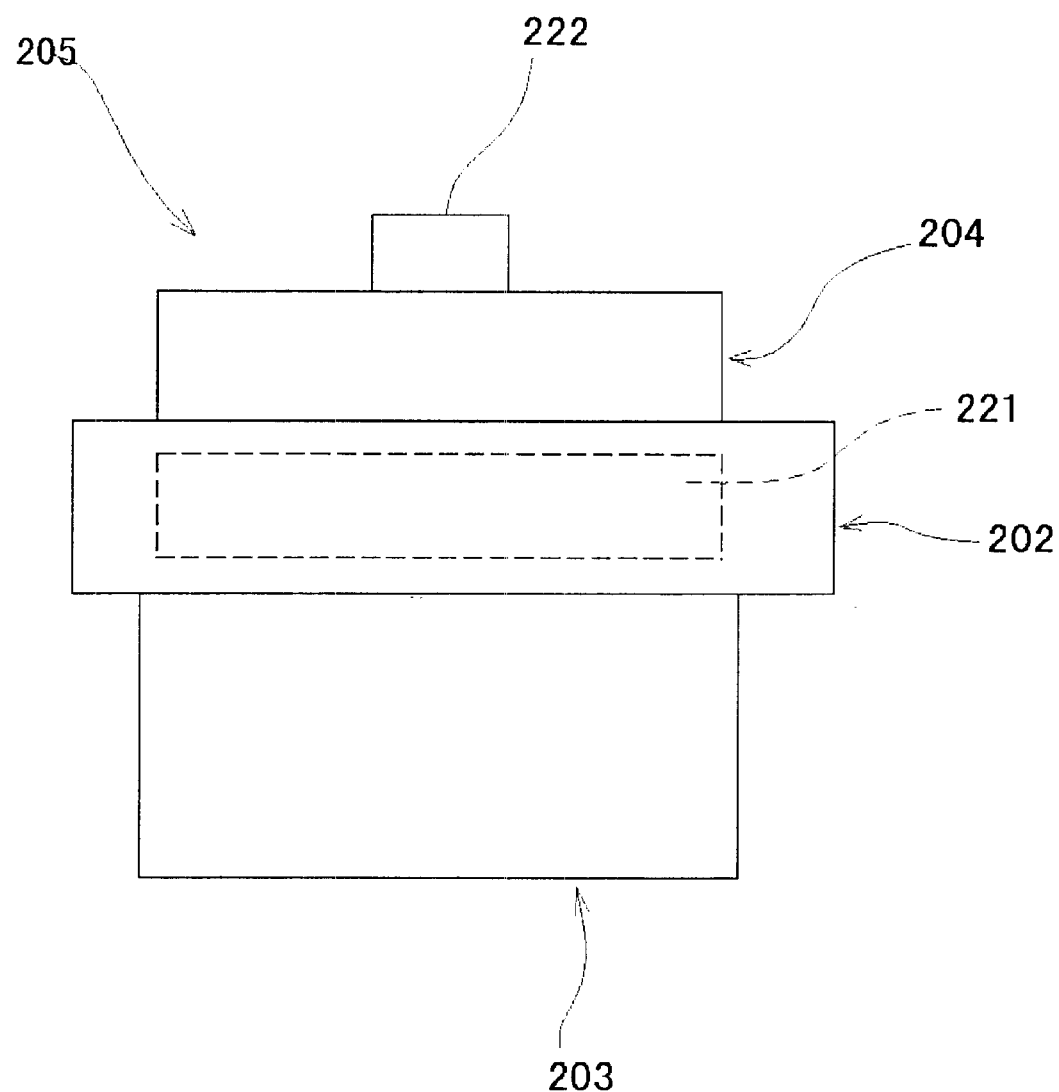
FIG. 16 is a front view showing an example of a centrifugal fluid pump that is used in the invention.
Figure 17:
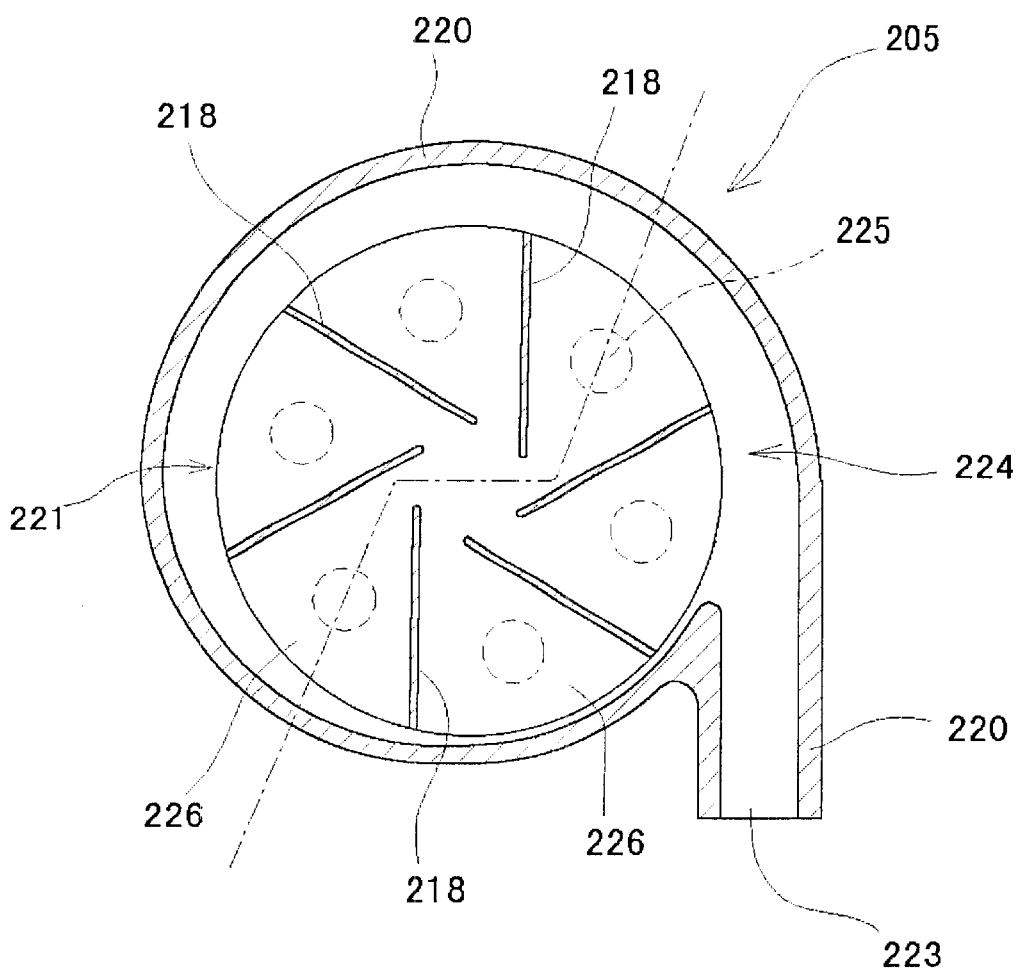
FIG. 17 is a cross-sectional view cut horizontally at the position of an impeller, showing the centrifugal fluid pump shown in FIG. 16.
Figure 18:
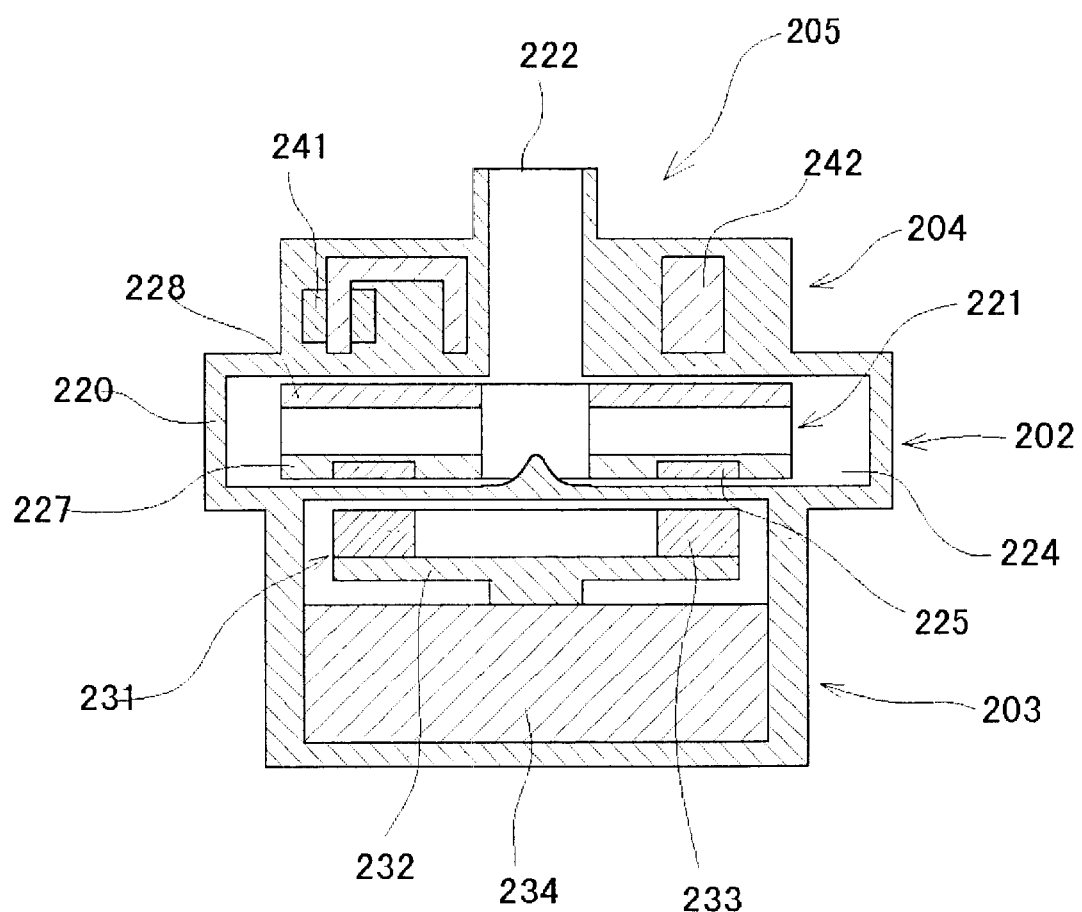
FIG. 18 is a vertical sectional view showing the centrifugal fluid pump shown in FIG. 16.
Figure 19:
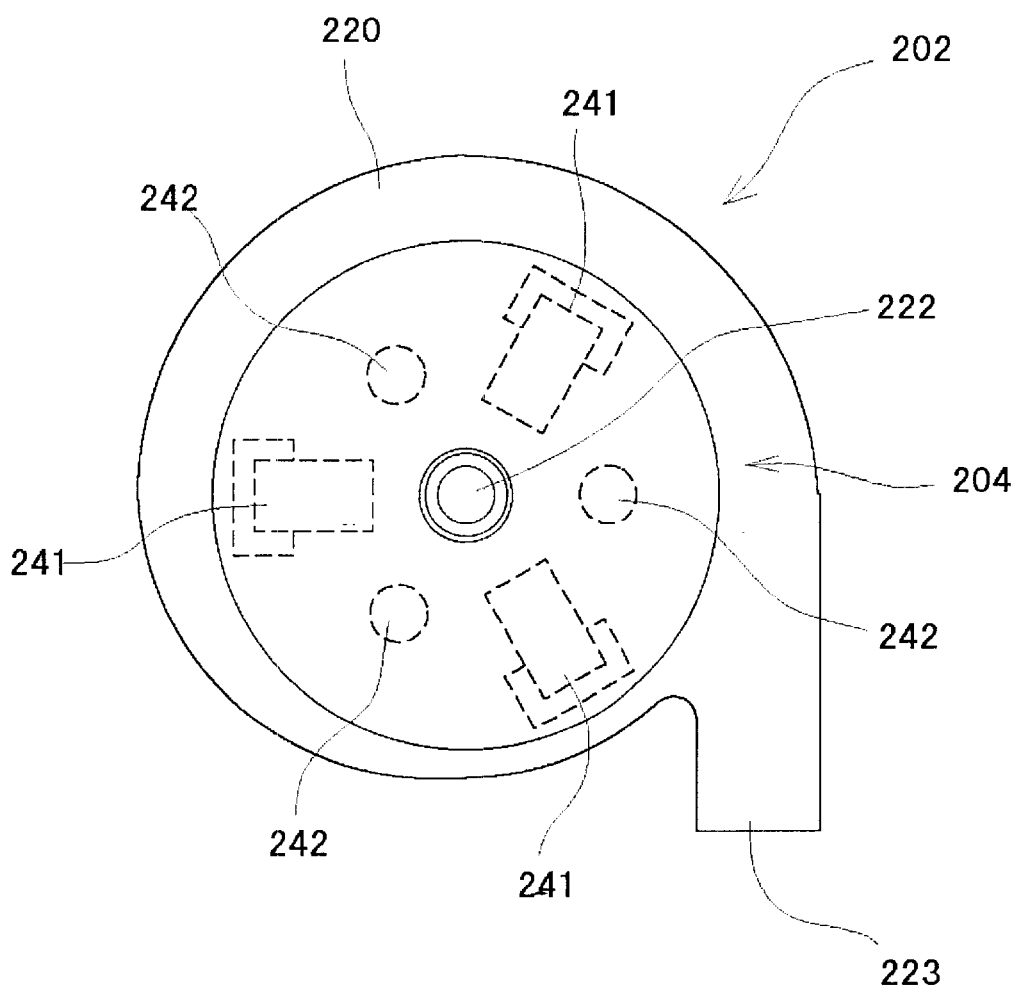
FIG. 19 is a plane view showing the centrifugal fluid pump shown in FIG. 16.

The control device 206 will be described below with reference to FIG. 15.

The control device 206 includes a motor driver having a power amplifier 252 for a magnetic coupling motor 234 and a motor control circuit 253; a magnetic bearing controller having a power amplifier 254 for the electromagnet 241, a sensor circuit 255 for the sensor 242 and a PID compensator 256 for the sensor 242; a first magnetic coupling abnormality detector 257 monitoring current to be supplied to the electromagnet 241 by the power amplifier 254; a second magnetic coupling abnormality detector 258 monitoring the motor-driving current to be supplied to the motor 234 by the power amplifier 252 and a signal indicating the number of rotations of the motor to be outputted thereto from the motor control circuit 253; and a control part 251. The control part 251 is electrically connected to the first magnetic coupling abnormality detector 257 and the second magnetic coupling abnormality detector 258. More specifically, the control part 251 is connected therewith such that signals are inputted to the control part 251 from the detectors 257, 258. The control part 251 is also electrically connected to the motor control circuit 253 of the motor driver and the power amplifier 254 of the magnetic bearing controller and has a function of controlling the motor control circuit 253 and the power amplifier 254. Further, the control device 206 includes a motor current abnormality detector 262, a motor rotations number abnormality detector 262, a detector 261 for detecting abnormality of number of rotations of motor and a temperature abnormality detector 266.

The control device 206 has a function of determining whether the impeller has the power swing (in other words, decoupling of magnetic coupling or decoupling between the impeller and the rotor) or not by utilizing a current value monitored by the function of monitoring the electric current flowing through the electromagnet, a value of the motor-driving current monitored by the function of monitoring the value thereof, and a number of rotations of the motor monitored by the function of monitoring the number of rotations thereof. The function of determining whether the impeller has the power swing is a function of determining whether the impeller and the rotor are decoupling. More specifically, the function of determining whether or not the impeller has the power swing determines that the impeller has the power swing when a current value monitored by the-function of monitoring the electric current flowing through the electromagnet is less than a first predetermined value or when a motor-driving current value monitored by the function of monitoring the motor-driving current is lower than a first predetermined motor-driving current value corresponding to the number of rotations of the motor monitored by the function of monitoring the number of rotations thereof.

In the function of determining whether or not the impeller has the power swing, the above-described two methods are used. To prevent the function of determining whether or not the impeller has the power swing from determining a normal state as an abnormal state, the two methods can be utilized effectively in combination.

The function of determining whether or not the impeller has the power swing has the first magnetic coupling abnormality detector 257 serving as a means for determining whether or not a current value monitored by the function of monitoring the electric current flowing through electromagnet is less than the first predetermined value.

Figure 20:
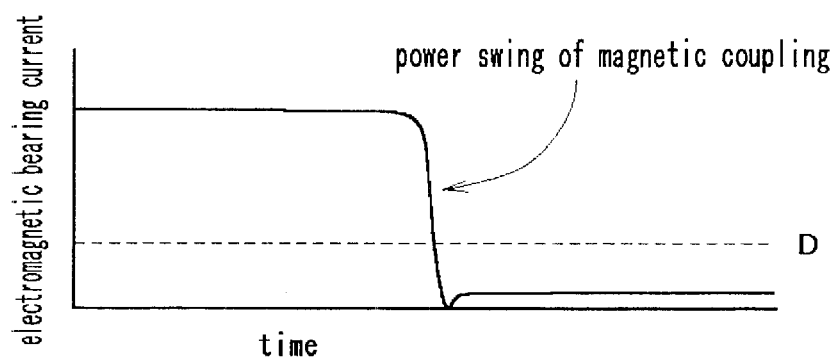
FIG. 20 is an explanatory view for explaining change of electric current flowing through a magnetic bearing when an impeller for use in the centrifugal fluid pump assembly has a power swing (power swing of magnetic coupling).

FIG. 20 is an explanatory view for explaining the change of electric current flowing through the magnetic bearing when the impeller has the power swing (power swing of coupling of magnetic bearing). When the magnetic coupling has the power swing, the impeller has an irregular displacement in the housing or is displaced away from the motor toward the electromagnet. Thus, the impeller is not attracted toward the motor and the value of the electric current flowing through the electromagnet decreases. When the electric current flowing through the electromagnet becomes lower than a threshold (D in FIG. 20), it is determined that the magnetic coupling is abnormal.

Figure 21:
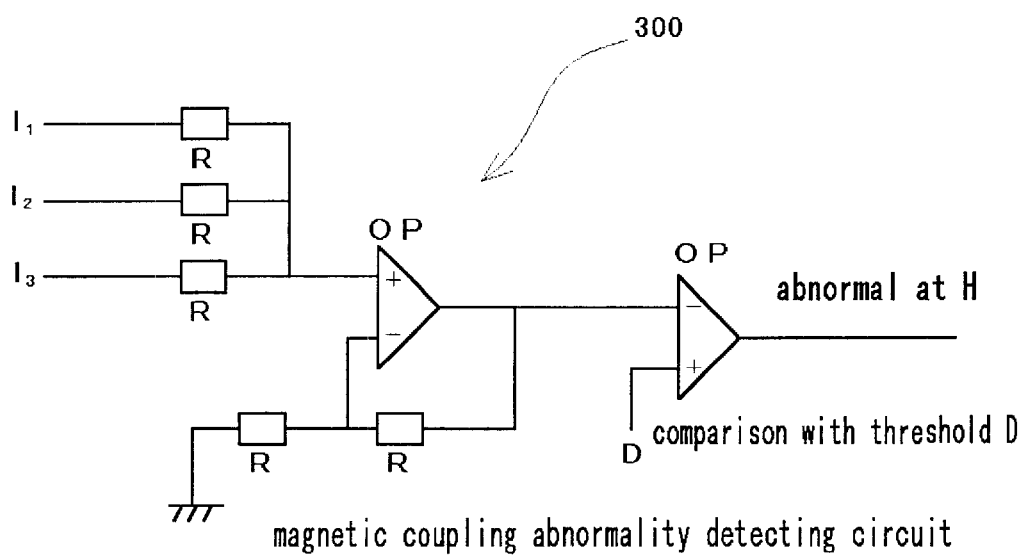
FIG. 21 is a block diagram showing an example of a circuit for detecting occurrence of the power swing (power swing of magnetic coupling) of the impeller for use in the centrifugal fluid pump assembly of the invention.

A circuit 300 shown in FIG. 21 is preferable as the first magnetic coupling abnormality detector 257 monitoring the electric current flowing through the electromagnet. FIG. 21 is a block diagram showing an example of a circuit for detecting occurrence of the power swing of the impeller (power swing of coupling of magnetic bearing) for use in the pump assembly of the invention.

In the circuit 300, current values (I 1, I 2, I 3) corresponding to the respective electromagnets (three in the embodiment) of the centrifugal pump for the magnetic bearing are monitored. The first operational amplifier performs an addition of the current values. When the added value is smaller than the threshold D (when output of second operational amplifier is H), it is determined that the impeller is abnormal. The detector for detecting the abnormality of the magnetic coupling is not limited to the circuit 300. For example, it is possible to use a detector that detects abnormality of each electric current flowing through the electromagnet when any one or two or more thereof are smaller than the threshold. Instead of the detector of the analog type, a detector of digital type may be used. As the value of electric current to be used in the detector as the information for determining whether the magnetic coupling is abnormal, it is possible to use an addition of electric current values in a predetermined period of time, an average of an addition of the electric current values in a predetermined period of time, and an average of the electric current values in a predetermined period of time.

In the case where the addition of electric current values in a predetermined period of time is used, digital processing is used. In the case where the average of the addition of electric current values in a predetermined period of time is used, digital processing is also used. In the case where the average of electric current values in a predetermined period of time is used, an analog circuit using a low-pass filter or digital processing can be also used.

The function of determining whether or not the impeller has the power swing has the second magnetic coupling abnormality detector 258 for determining whether a motor-driving current value monitored by the function of monitoring the value thereof is lower than a first predetermined motor-driving current value corresponding to the number of rotations of the motor monitored by the function of monitoring the number of rotations thereof.

Figure 22:
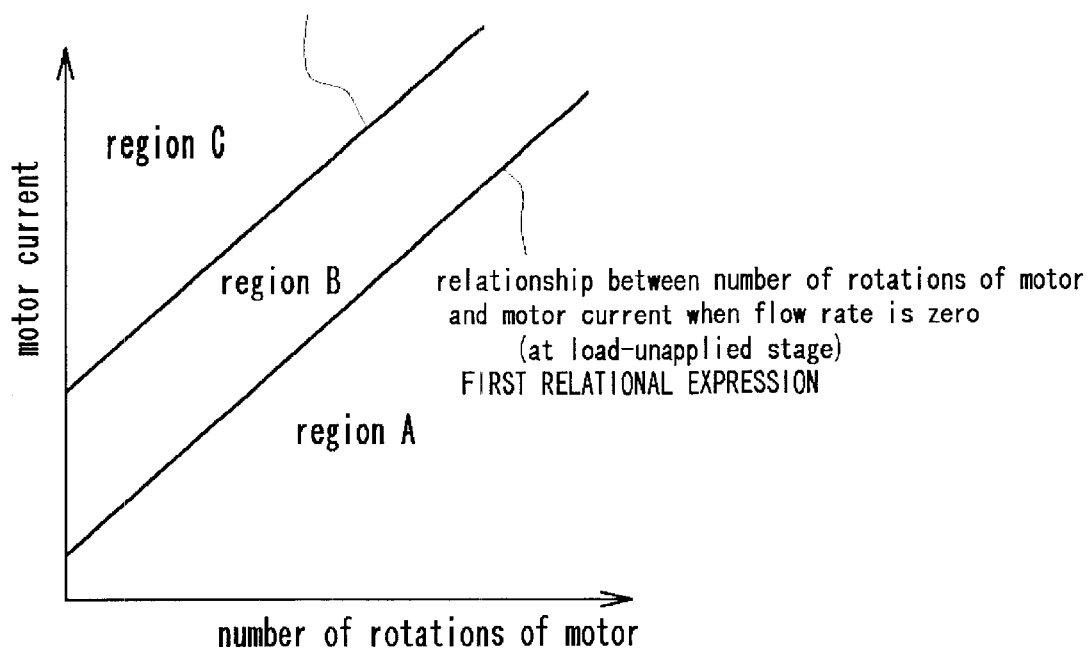
FIG. 22 is an explanatory view for explaining the relationship between the number of rotations of the motor and electric current applied thereto in the centrifugal fluid pump assembly of the invention.

FIG. 22 is an explanatory view for explaining the relationship between the number of rotations of the motor and electric current applied thereto in the pump assembly of the invention. The present inventors have confirmed in experiments that the value of electric current applied to the motor in each number of rotations of the motor is located in a region B of FIG. 22 when the impeller rotates floatingly in a normal state and moves to a region A of FIG. 22 when the magnetic coupling has the power swing. Thus, when the value of the electric current is located in the region A of FIG. 22, it is determined that the magnetic coupling is abnormal.

Figure 23:
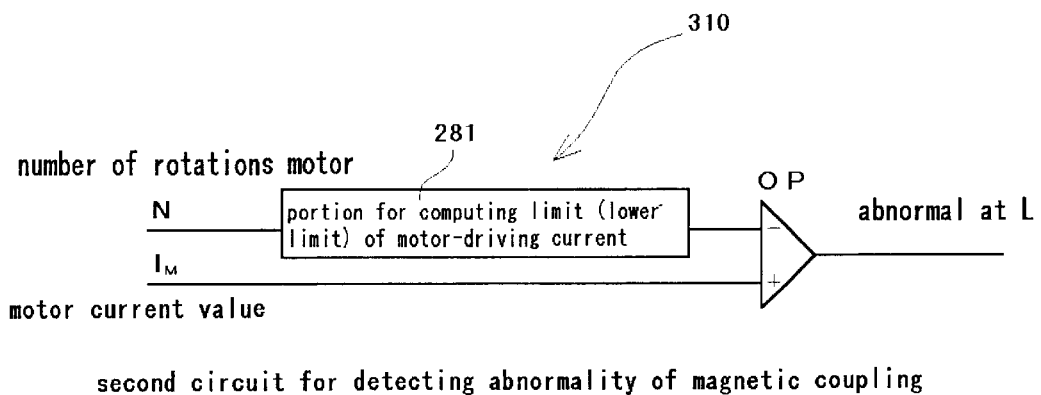
FIG. 23 is a block diagram showing an example of a second circuit, for detecting occurrence of the power swing (second power swing of magnetic coupling) of the impeller, for use in the centrifugal fluid pump assembly of the invention.

The following case is determined as abnormal: the case where the value of electric current applied to the motor is lower than the value of electric current applied thereto at the time when the impeller rotates floatingly in a sealed state (flow rate 0 L/min), with blood having a predetermined viscosity (for example, $3 \times 10^{-3}$ Pa.s) filled in a blood pump such as an artificial heart. Values of electric currents applied to the motor were measured when the motor was rotated in varied number of rotations in the above-described state. A relational expression (first relational expression) to be used to determine whether or not the magnetic coupling is abnormal was obtained from measured values. The relational expression was a primary regression equation obtained by using method of least square. The relational expression may be a regression equation of secondary or more degrees A circuit 310 as shown in FIG. 23 is preferably used as the second magnetic coupling abnormality detector 258. FIG. 23 is a block diagram showing an example of a second circuit for detecting occurrence of the power swing of the impeller (second power swing of magnetic coupling) for use in the pump assembly of the invention.

Figure 24:
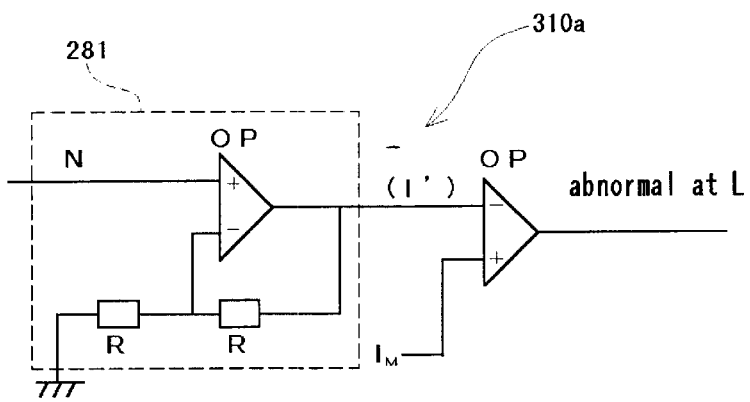
FIG. 24 is a block diagram showing an embodiment of the second circuit, for detecting occurrence of the power swing (second power swing of magnetic coupling) of the impeller, for use in the centrifugal fluid pump assembly of the invention.

In the circuit 310, a current value at which the magnetic coupling is determined as abnormal is computed from a monitored number of rotations of the motor. A computed current value is compared with a monitored value of electric current applied to the motor. If the monitored value of the electric current applied to the motor is lower than the computed current value, it is determined that the magnetic coupling is abnormal. A circuit 281 for computing the current value has a function of storing a relational expression (which is used to determine whether or not the impeller has the power swing) between the number of rotation of the motor and the value of the motor-driving current. For example, the circuit 281 has a function of storing the relational expression (first relational expression) which is used to determine whether or not the magnetic coupling is abnormal or storing a current value computing equation derived from the first relational expression. The circuit 281 has also a function of computing a limit current value (lower limit current value) by using the stored relational expression or by using the current value computing equation and an inputted number of rotations of the motor. More specifically, using an inputted digital signal indicating the number of rotations of the motor or converting an analog signal into the digital signal, the digital signal indicating the number of rotations of the motor is inputted to a computing portion, and the computing portion computes the limit current value (lower limit current value) from the stored first relational expression which is used to determine whether or not the magnetic coupling is abnormal or the current value computing equation derived from the first relational expression. Then, a digital-to-analog conversion of the computed current value is performed, and then an analog value is inputted to a comparator to compare the monitored value of the electric current applied to the motor with the computed current value. When the monitored value of the current applied to the motor is smaller than the computed current value, it is determined that the magnetic coupling is abnormal. The second magnetic coupling abnormality detector 258 is not limited to the digital type. For example, as shown in FIG. 24, it may be of analog type. In an analog circuit 310a of FIG. 24, an output I' of a computing portion 281 for computing a value of electric current applied to the motor is supposed to be proportional to the number of rotations of the motor.

As the value of the motor electric current which is used in the magnetic coupling abnormality detector as the information for determining whether the magnetic coupling is abnormal, it is possible to use an addition of electric current values in a predetermined period of time, an average of an addition of electric current values in a predetermined period of time, and an average of electric current values in a predetermined period of time.

In the case where the addition of electric current values in a predetermined period of time is used, digital processing is used. In the case where the average of the addition of electric current values in a predetermined period of time is used, digital processing is also used. In the case where the average of electric current values in a predetermined period of time is used, an analog circuit using a low-pass filter or digital processing can be also used.

Figure 25:
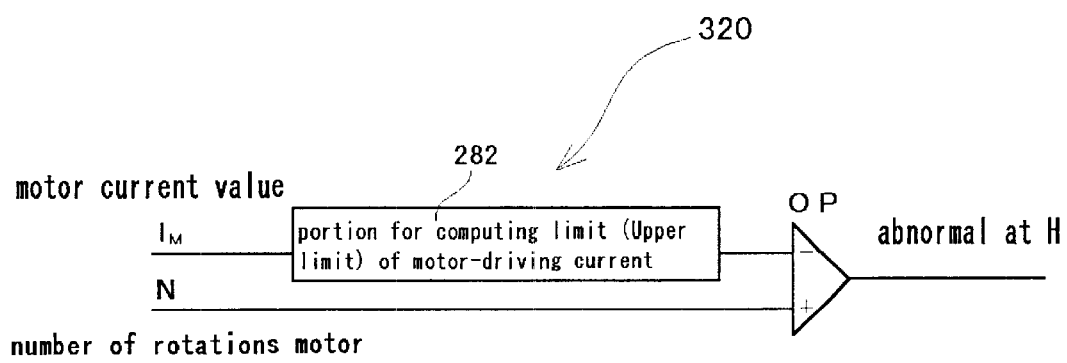
FIG. 25 is a block diagram showing another example of the second circuit, for detecting occurrence of the power swing (second power swing of magnetic coupling) of the impeller, for use in the centrifugal fluid pump assembly of the invention

The second magnetic coupling abnormality detector 258 is not limited to the above-described type. For example, a circuit 320 as shown in FIG. 25 may be used. FIG. 25 is a block diagram showing another example of the second circuit (second detecting method of power swing of magnetic coupling) for detecting occurrence of the power swing of the impeller for use in the pump assembly of the invention.

In the circuit 320, a number of rotations of the motor at which the magnetic coupling is determined as abnormal is computed from a monitored value of electric current applied to the motor. The computed number of rotations of the motor is compared with a monitored number of rotations thereof. If the monitored number of rotations of the motor is larger than the computed number of rotations, it is determined that the magnetic coupling is abnormal. In this case, the second magnetic coupling abnormality detector 258 does not have the circuit 281 for computing the electric current value, but a circuit 282 for computing the number of rotations of the motor. The circuit 282 has a function of storing a relational expression between the number of rotations of the motor to be used to determined whether or not the impeller has the power swing and the value of the motor-driving current. For example, the circuit 282 has a function of storing the relational expression (first relational expression) to be used to determine whether or not the magnetic coupling is abnormal or storing an equation, for computing the number of rotations of the motor, derived from the first relational expression. The circuit 282 has also a function for computing a limit number of rotations (upper limit number of rotations) by using the stored relational expression or by using the equation for computing the number of rotations of the motor and an inputted value of electric current to be applied to the motor. More specifically, an inputted current value signal is converted into a digital signal, the digital signal indicating the current value is inputted to a computing portion, and the computing portion computes a number of rotations (limit number of rotations, upper limit number of rotations) from the stored first relational expression to be used to determine whether or not the magnetic coupling is abnormal or the equation, for computing the number of rotations, derived from the first relational expression. Then, a digital-to-analog conversion of the computed number of rotations is performed and then an analog value is inputted to a comparator to compare the computed number of rotations and the monitored number of rotations of the motor. When the monitored number of rotations of the motor is larger than the computed number of rotations, it is determined that the magnetic coupling is abnormal.

As the number of rotations of the motor which is used in the magnetic coupling abnormality detector as the information for determining whether the magnetic coupling is abnormal, it is possible to use an addition of number of rotations of the motor in a predetermined period of time, an average of an addition of number of rotations thereof in a predetermined period of time, and an average of number of rotations thereof in a predetermined period of time.

In the case where the addition of number of rotations of the motor in a predetermined period of time is used, digital processing is used. In the case where the average of the addition of number of rotations thereof in a predetermined period of time is used, digital processing is also used. In the case where the average of number of rotations thereof in a predetermined period of time is used, an analog circuit using a low-pass filter or digital processing can be used.

It is preferable that the control device 206 has a power swing cancellation function (in other words, decoupling cancellation function) to be executed when it is determined that the impeller has the power swing (in other words, power swing of magnetic coupling or decoupling between the impeller and the rotor) by the function of determining whether the impeller has the power swing.

The present inventors have confirmed that the magnetic coupling can be frequently recovered from the power swing by stopping the rotation of the motor or rotating it at a low speed (for example, 300 rpm).

As the power swing cancellation function, it is preferable to use a temporary stopping type that has a function of suspending and resuming the rotation of the motor after the function of determining whether the impeller has the power swing (in other words, magnetic coupling has power swing) has determined that the impeller has the power swing.

Figure 26:
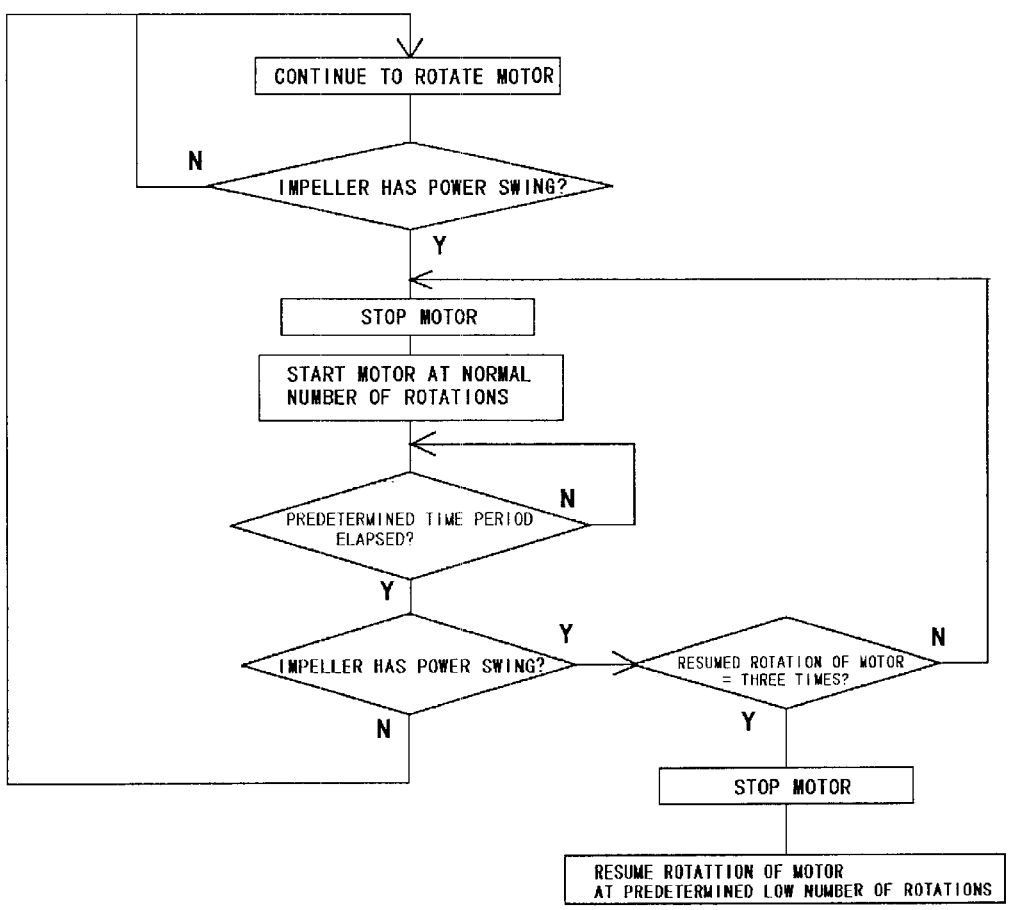
FIG. 26 is a flowchart showing an example of a power swing cancellation function for use in the centrifugal fluid pump assembly of the invention.

The power swing cancellation function of temporary stopping type can be executed, as shown in a flowchart of FIG. 26. FIG. 26 is the flowchart showing an example of the power swing cancellation function (in other words, decoupling cancellation function) for use in the pump assembly of the invention.

In the power swing cancellation function of temporary stopping type, as shown in FIG. 26, it is determined whether or not the impeller has the power swing during the rotation of the motor. If it is determined that the impeller has the power swing, the rotation of the motor is stopped and started again at a normal number of rotations. It is determined again that the impeller has the power swing after a predetermined period of time elapses, for example, 10–20 seconds elapse. If it is determined again that the impeller does not have the power swing, the rotation of the motor is continued. Let it be supposed that the impeller cannot be recovered from the power swing even though the rotation of the motor is stopped or resumed several times (for example, 3–10 times, three times in the embodiment). In this case, after the rotation of the motor is stopped, the rotation of the motor is started at a predetermined number of rotations, for example, 1000–1500 rpm.

Figure 27:
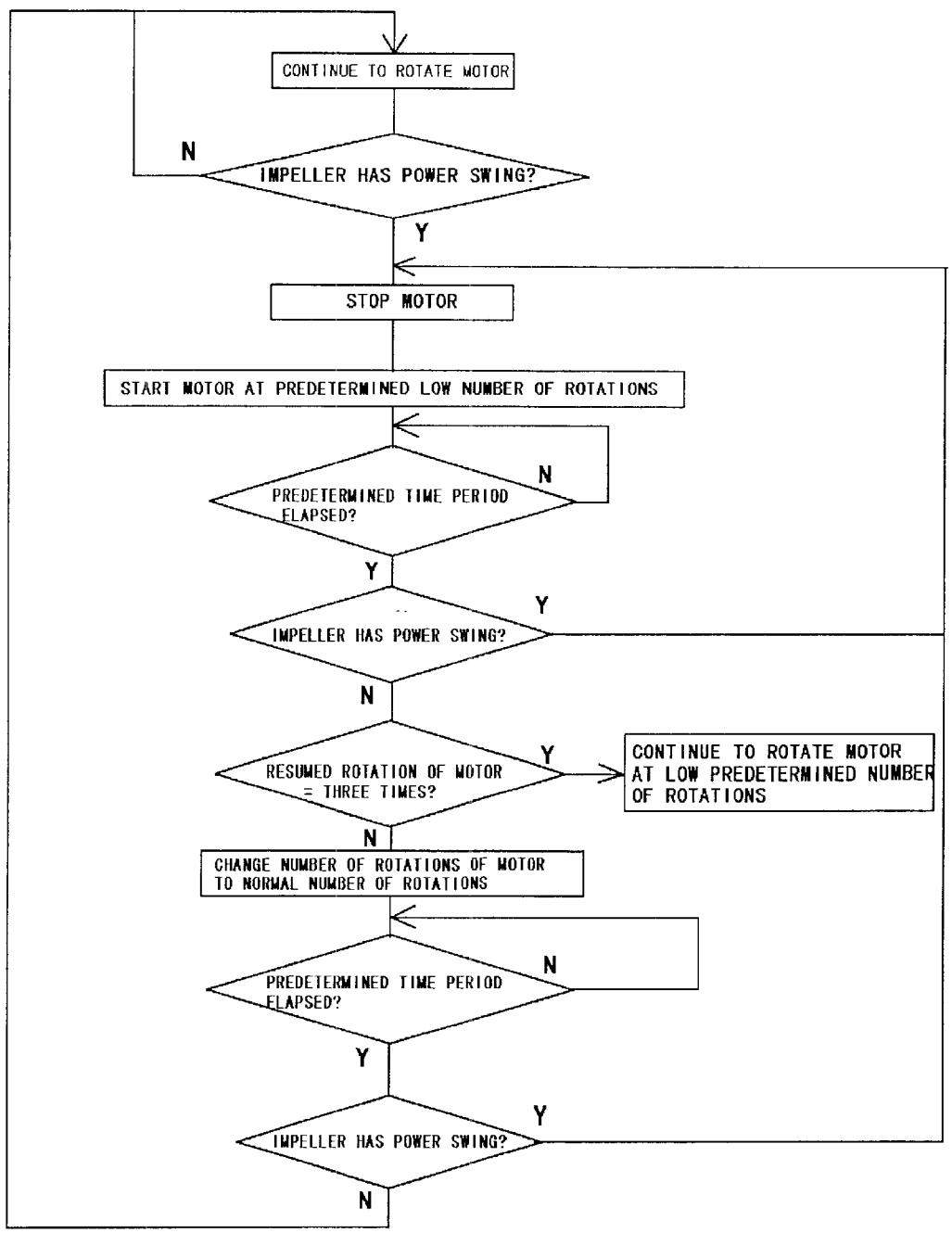
FIG. 27 is a flowchart showing another example of a power swing cancellation function for use in the centrifugal fluid pump assembly of the invention.

The rotation of the motor may be controlled as follows: Referring to FIG. 27, after the impeller is recovered from the power swing, the number of rotations of the motor is not increased to the normal one but to the predetermined number of rotations (for example, 1000–1500 rpm). After a predetermined period of time (for example, 10–300 seconds) elapses, it is determined whether or not the impeller has the power swing. If it is determined that the impeller does not have the power swing, the motor is rotated at the normal number of rotations and the rotation thereof is continued. In this case, if the impeller has the power swing several times (for example, 3–10 times, three times in the embodiment) repeatedly after the motor is rotated at the normal number of rotations, the motor is continuously rotated at the predetermined number of rotations (for example, 1000–1500 rpm).

As the power swing cancellation function, it is preferable to use a temporary low-speed type that has a function of rotating the motor at a low speed (for example, 100–500 rpm) for a predetermined period of time (2–10 seconds) and then increasing the number of rotations of the motor after the function of determining whether the impeller has a power swing has determined that the impeller has the power swing.

Figure 28:
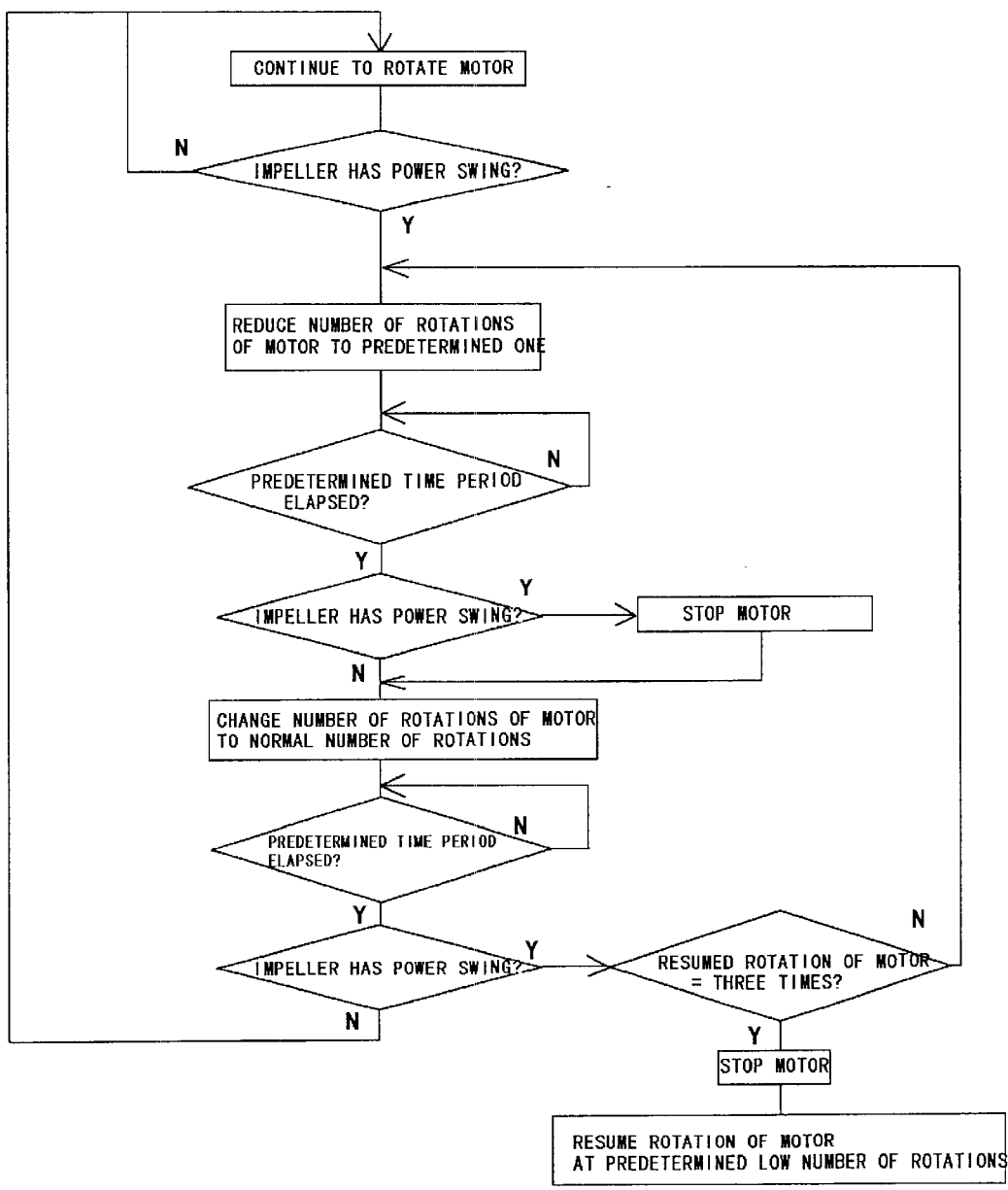
FIG. 28 is a flowchart showing still another example of a power swing cancellation function for use in the centrifugal fluid pump assembly of the invention.

The power swing cancellation function of temporary low-speed tripe can be executed, as shown in a flowchart of FIG. 28. In the embodiment of the power swing cancellation function of temporary low-speed type, if the impeller cannot be recovered from the power swing even though the motor is rotated at a low speed temporarily, the power swing cancellation function of temporary stopping type of stopping the motor temporarily is used in combination. Referring to FIG. 28, it is determined whether or not the impeller has the power swing during the rotation of the motor. If it is determined that the impeller has the power swing, the number of rotation of the motor is reduced to a predetermined one (for example, 100–500 rpm). It is determined whether or not the impeller has the power swing after a predetermined period of time (for example, 2–20 seconds) elapses. If the impeller does not have the power swing, the number of rotations of the motor is increased to the normal one and the rotation thereof is continued. If the impeller cannot be recovered from the power swing even though the number of rotations of the motor is reduced, the rotation thereof is stopped and resumed at the normal number of rotations again. It is determined again whether or not the impeller has the power swing after a predetermined period of time (for example, 2–10 seconds) elapses. In the case where the impeller cannot be recovered from the power swing even though the rotation of the motor is stopped and resumed several times (for example, 3–10 times, three times in the embodiment), the rotation of the motor is stopped and then started at a predetermined number of rotations (for example, 100–500 rpm).

Figure 29:
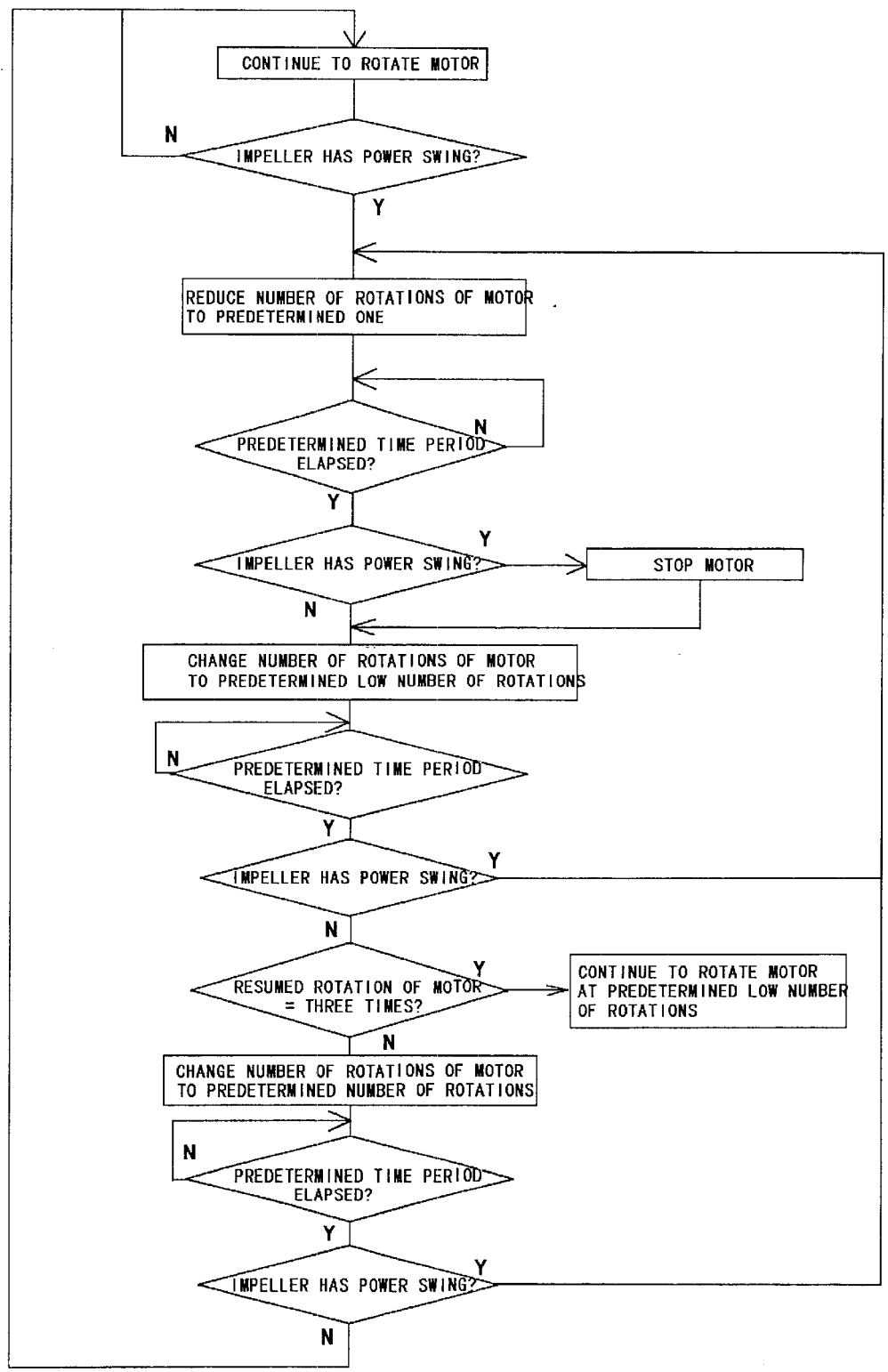
FIG. 29 is a flowchart showing still another example of a power swing cancellation function for use in the centrifugal fluid pump assembly of the invention

The following control may be executed, as shown in FIG. 29. That is, after the impeller is recovered from the power swing, the number of rotations of the motor is not increased to the normal one but to the predetermined one (for example, 100–500 rpm). Then, it is determined again whether or not the impeller has the power swing after a predetermined period of time (for example, 10–300 seconds) elapses. If the impeller does not have the power swing, the number of rotations of the motor is increased to the normal one and the rotation thereof is continued. In this case, if the power swing occurs several times (for example, 3–10 times, three times in the embodiment) repeatedly after the number of rotations of the motor is increased to the normal one, the rotation of the motor is continued at the predetermined number of rotations (for example, 100–500 rpm).

It is preferable that the control device 206 has a function of determining whether the motor rotates in a high load-applied state. The function of determining whether the motor rotates in a high load-applied state determines that the motor rotates in a high load-applied state when the value of the motor-driving current monitored by the function of monitoring the value thereof is larger than a second predetermined motor-driving current value corresponding to the number of rotations of the motor monitored by the function of monitoring the number of rotation thereof.

The function of determines whether the motor rotates in a high load-applied state stores a relational expression between the number of rotations of the motor and the value of the motor-driving current. The relational expression is used to determine whether the motor rotates in a high load-applied state.

As described above, the value of current applied to the motor in each number of rotations of the motor is located in the region B of FIG. 22 when the impeller rotates floatingly in a normal state, but the value of current applied thereto may move to a region B or C of FIG. 22 when the following abnormalities occur: formation of thrombus in the pump chamber, abnormal floating of the impeller, penetration of foreign matter into the motor, failure of the bearing of the motor, failure of the motor control circuit, and the like. The case where the relationship between the number of rotations of the motor and the value of the electric current applied to the motor is located in the region C of FIG. 22. More specifically, the following case is determined as abnormal: the case where the value of electric current applied to the motor is more than the value of electric current applied thereto at the time when the impeller rotates floatingly at a predetermined flow rate (for example, 10–15L/min), with blood having a viscosity of $6 \times 10^{-3}$Pa.s filled in a blood pump such as an artificial heart. The state where the motor rotates in a high load-applied state can be detected by a method (circuit) similar to that of detecting the abnormality of the magnetic coupling.

Figure 30:
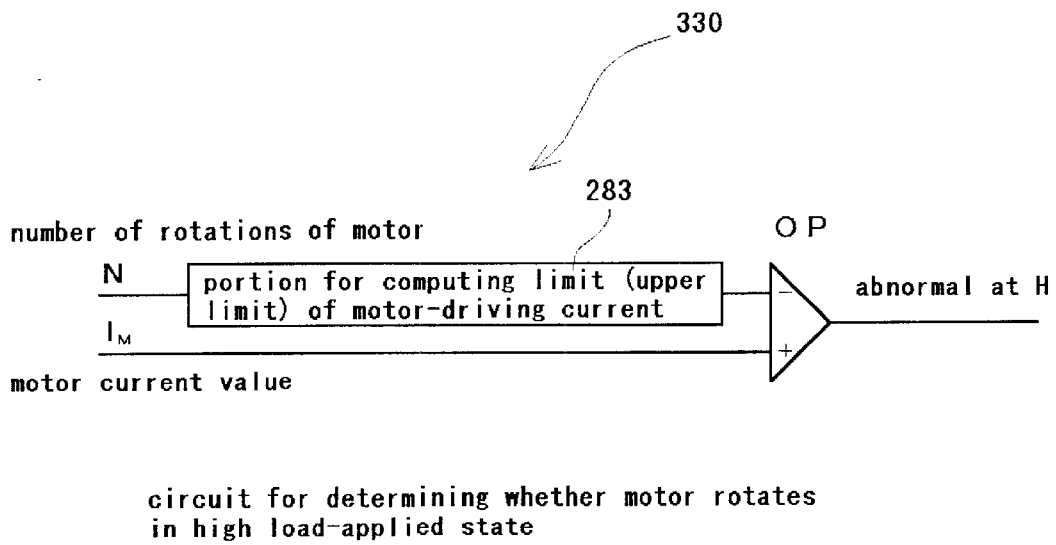
FIG. 30 is a block diagram showing an example of a circuit, for determining whether the motor rotates in a high load-applied state, for use in the centrifugal fluid pump assembly of the invention.

A circuit 330 as shown in FIG. 30 is preferable as a motor abnormality detector 263 serving as a means for determining g whether the motor rotates in a high load-applied state. FIG. 30 is a block diagram showing an example of a circuit, for determining whether the motor rotates in a high load-applied state, for use in the pump assembly of the invention.

In the circuit 330, a current value at which the motor rotates in a high load-applied applied state is computed from a monitored number of rotations of the motor. The computed current value is compared with a monitored value of electric current applied to the motor. If the monitored value of the electric current applied to the motor is higher than the computed current value, it is determined that the motor rotates is in a high load-applied state. A circuit 283 for computing the current value at which the motor rotates in a high load-applied state has a function of storing a relational expression between the number of rotations of the motor and the value of the motor-driving current (the relational expression is used to determine whether or not the motor rotates is in a high load-applied state). For example, the circuit stores the relational expression (second relational expression) to be used to determine whether the motor rotates is in a high load-applied state or stores a current value computing equation derived from the second relational expression. The circuit 283 has also a function of computing a limit current value (upper limit current value) by using the stored relational expression or by using the current value computing equation and an inputted number of rotations of the motor. More specifically, using an inputted digital signal indicating the number of rotations of the motor or converting an analog signal into a digital signal, the digital signal indicating the number of rotations of the motor is inputted to a computing portion, and the computing portion computes the limit current value (upper limit current value) from the stored second relational expression to be used to determine whether the motor rotates is in a high load-applied state or the current value computing equation derived from the second relational expression. Then, a digital-to-analog conversion of the computed current value is performed and then an analog value is inputted to a comparator to compare the monitored value of the current applied to the motor with the computed current value. When the monitored value of the current applied to the motor is larger than the computed current value, it is determined that the motor rotates is in a high load-applied state.

As the value of the motor electric current and the number of rotations of the motor both to be used in the detector in detecting whether the motor rotates is in a high load-applied state, it is possible to use an addition of electric current values or that of the number of rotations of the motor in a predetermined period of time, an average of an addition of electric current values or that of the number of rotations thereof in a predetermined period of time, and an average of electric current values or that of the number of rotations thereof in a predetermined period of time.

In the case where the addition of electric current values in a predetermined period of time is used, digital processing is used. In the case where the average of the addition of electric current values in a predetermined period of time is used, digital processing is also used. In the case where the average of electric current values in a predetermined period of time is used, an analog circuit using a low-pass filter or digital processing can be also used.

Figure 31:
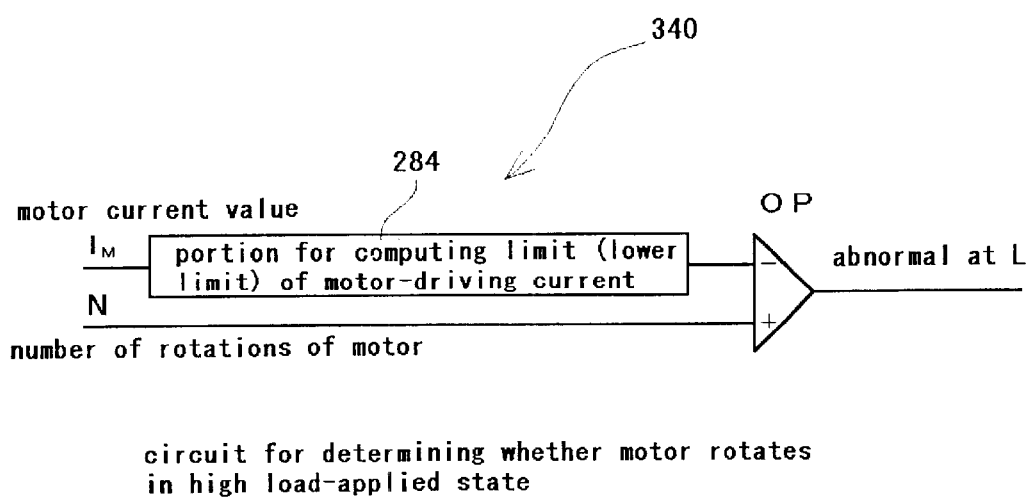
FIG. 31 is a block diagram showing another example of a circuit, for determining whether the motor rotates in a high load-applied state, for use in the centrifugal fluid pump assembly of the invention.

The motor abnormality detector 263 is not limited to the above-described type. For example, a circuit 340 as shown in FIG. 31 may be used. FIG. 31 is a block diagram showing another example of a circuit, for determining whether the motor rotates is in a high load-applied state, for use in the pump assembly of the invention.

In the circuit 340, a predetermined number of rotations of the motor at which it is determined that the motor rotates is in a high load-applied state is computed from a monitored value of electric current applied to the motor. The computed number of rotations is compared with a monitored number of rotations of the motor. If the monitored number of rotations of the motor is smaller than the computed number of rotations, it is determined that the motor rotates is in a high load-applied state. Therefore, the circuit of FIG. 31 does not have the circuit 283 for computing the value of the electric current applied to the motor but has a circuit 284 for computing the number of rotations of the motor. The circuit 284 for computing the number of rotations of the motor has a function of storing a relational expression (used to determine whether the motor rotates is in a high load-applied state) between the number of rotations of the motor and the value of the motor-driving current. For example, the circuit 284 has a function of storing the relational expression (second relational expression) to be used to determine whether the motor rotates is in a high load-applied state or storing an equation, for computing the number of rotations of the motor, derived from the second relational expression. The circuit 284 has also a function for computing a limit number of rotations (lower limit number of rotations by using the stored relational expression or by using the equation for computing the number of rotations of the motor and an inputted value of electric current applied to the motor. More specifically, an inputted signal, indicating the number of rotations of the motor, is converted into a digital signal, the digital signal indicating the value of the electric current applied to the motor is inputted to a computing portion, and the computing portion computes the number of rotations (limit number of rotations, lower limit number of rotations from the stored second relational expression to be used to determine whether the motor rotates is in a high load-applied state or the equation, for computing the number of rotations, derived from the second relational expression. Then, a digital-to-analog conversion of the computed number of rotations is performed and then an obtained analog value is inputted to a comparator to compare the computed number of rotations and the predetermined number of rotations of the motor. When the predetermined number of rotations of the motor is smaller than the computed number of rotations, it is determined that the motor rotates is in a high load-applied state.

In the case where the addition of number of rotations of the motor in a predetermined period of time is used, digital processing is used. In the case where the average of the addition of number of rotations thereof in a predetermined period of time is used, digital processing is also used. In the case where the average of number of rotations thereof in a predetermined period of time is used, an analog circuit using a low-pass filter or digital processing can be used.

It is preferable that the control device 206 has a function of monitoring an output value of the impeller position sensor and a function of determining whether the impeller position is abnormal. The function of determining whether the impeller position is abnormal determines that the impeller position is abnormal when an output value of the function of monitoring the output value of the impeller position sensor is more than a first predetermined stored value or less than a second predetermined stored value.

An output of a magnetic bearing position sensor indicates the floating position of the impeller in its axial direction. The control device controls the floating of the impeller such that the output of the magnetic bearing position sensor is zero. If the circuit of the magnetic bearing position sensor becomes abnormal or a foreign matter such as thrombus is formed in the pump chamber, the output value of the magnetic bearing position sensor is away from zero. Thus, when the output value of the magnetic bearing position sensor becomes larger than a given value, it is determined that the impeller position is abnormal (first abnormality of magnetic bearing).

Figure 32:
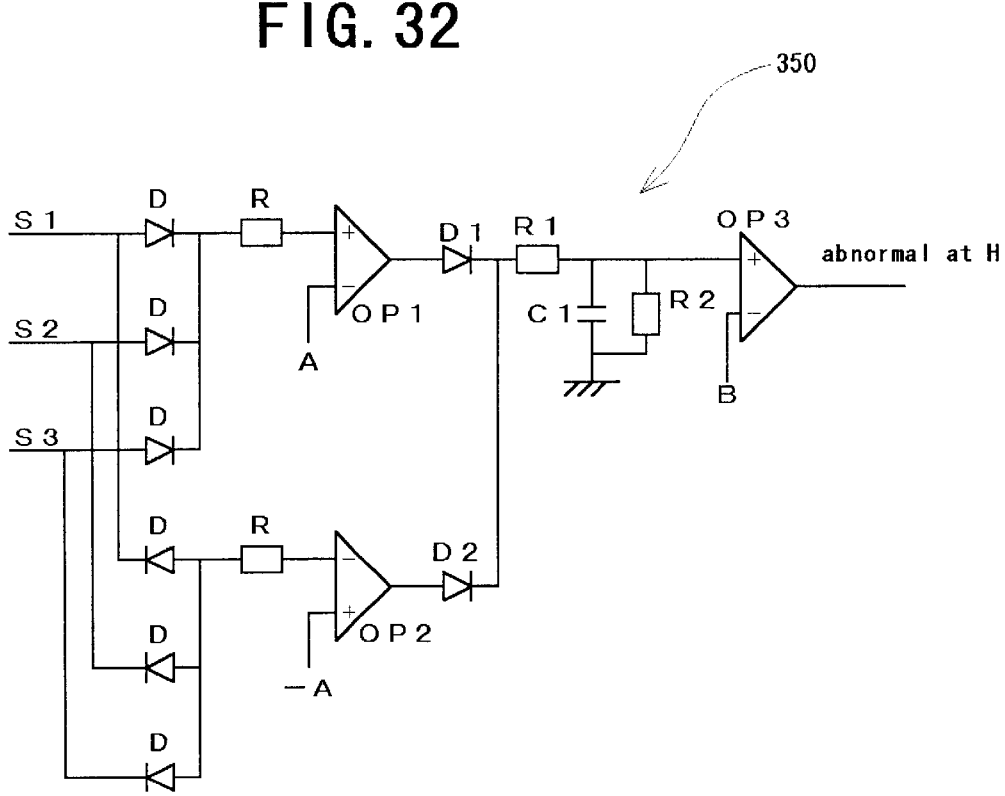
FIG. 32 is a block diagram showing an example of a circuit, for detecting abnormality of the position of the impeller (magnetic bearing), for use in the centrifugal fluid pump assembly of the invention.

As a detector 265 for detecting abnormality in the control of the magnetic bearing is used to detect abnormality (first abnormality of magnetic bearing) of the position of the impeller. As the detector 265, a circuit 350 as shown in FIG. 32 can be used. FIG. 32 is a block diagram showing an example of a circuit, for detecting abnormality abnormality of magnetic bearing) of the position of the impeller, for use in the pump assembly of the invention Outputs (S1, S2, S3) of three sensors are used in the control device 200. In the circuit 350, an operational amplifier OP1 compares the outputs of the sensors with a threshold A, and an operational amplifier OP2 compares the outputs of the sensors with a threshold -A. The operational amplifiers OP1, OP2 output a positive voltage, respectively when the outputs of the sensors exceed the threshold, whereas the operational amplifiers OP1, OP2 output a negative voltage, respectively when the outputs of the sensors do not exceed the threshold. Diodes D1 and D2 prevent the output of the operational amplifiers OP1, OP2 from being applied to a resistor Rd. The output of the positive voltage is inputted to a non-inverting terminal of an operational amplifier OP3 through a primary low-pass filter composed of a resistor R1 and a capacitor C2. That is, a voltage proportional to an integrated period of time of the positive-voltage output of the operational amplifiers OP1, OP2 is inputted to the non-inverting terminal of the operational amplifier OP3. The voltage of the non-inverting terminal of the operational amplifier OP3 is compared with the threshold B to determine whether or not the position of the impeller is abnormal. A resistor P2 serves as a means for discharging the non-inverting terminal of the operational amplifier OP3. When an abnormal of the output of the sensor does not have continuation, it is not determined that the position of the impeller is abnormal.

In the circuit 350, the output of each sensor is monitored to execute a determination about abnormality. Instead, it is possible to monitor the sum of the outputs of the respective sensors to execute a determination about abnormality.

In addition to the method of determining that the position of the impeller is abnormal when the output of any one of the sensors is abnormal as performed in the circuit 350 monitoring the sensors, it is possible to adopt a method of determining that the position of the impeller is abnormal only when the outputs of two or more sensors are abnormal.

As the value of the output of the sensor to be used as the information for the detector for detecting abnormality in the control of the magnetic bearing, it is possible to use an addition of output values in a predetermined period of time, an average of an addition of the output values in a predetermined period of time, and an average of the output values in a predetemiined period of time.

Figure 33:
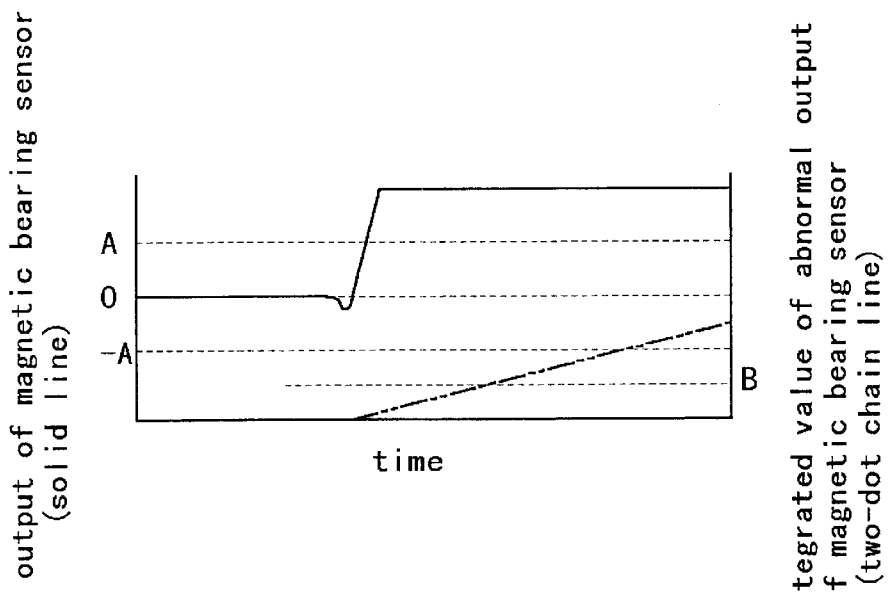
FIG. 33 is an explanatory view for explaining the relationship between time and an output of a magnetic bearing sensor as well as an integrated value of abnormal outputs of the magnetic bearing sensor when the magnetic bearing is abnormal (abnormality of impeller position in the centrifugal fluid pump assembly)
Figure 34:
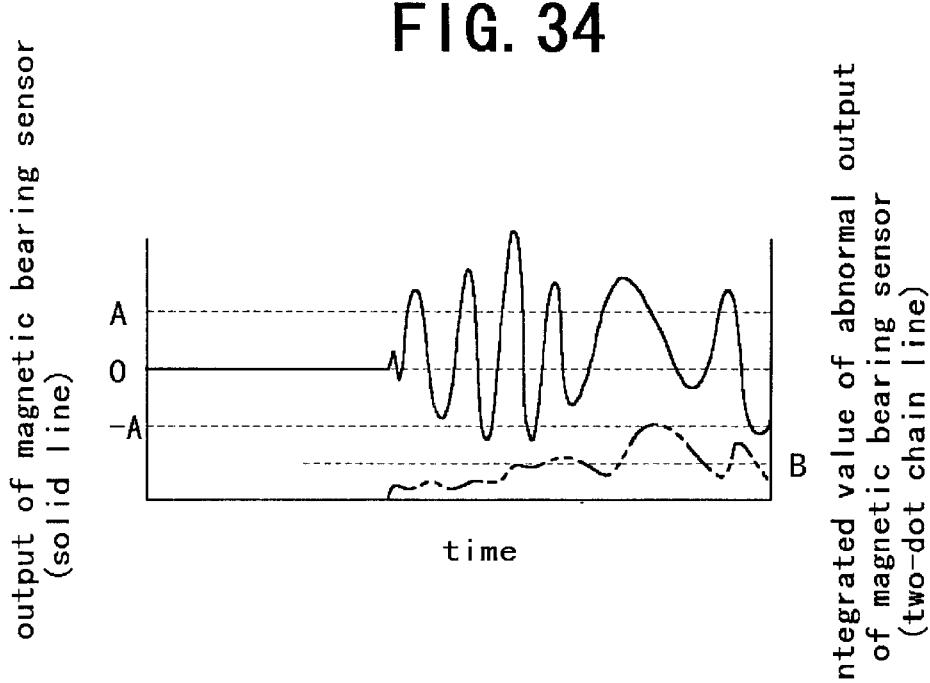
FIG. 34 is an explanatory view for explaining the relationship between time and an output of a magnetic bearing sensor as well as an integrated value of abnormal outputs of the magnetic bearing sensor when the magnetic bearing has a different type of abnormality (abnormality of impeller position) in the centrifugal fluid pump assembly.

FIGS. 33 and 34 are explanatory views for explaining the relationship between time and an output of the magnetic bearing sensor and an integrated value of abnormal outputs of the magnetic bearing sensor when the magnetic bearing is abnormal (abnormality of impeller position) in the pump assembly. 20

More specifically, FIG. 33 shows the output of the sensor with a solid line in a static abnormal state where the impeller is stationary at the motor side. A two-dot chain line of FIG. 33 shows the voltage of the non-inverting terminal of the operational amplifier OP3. when the voltage (two-dot chain line) of the non-inverting terminal of the operational amplifier OP3 exceeds the threshold B, it is determined that the magnetic bearing is abnormal.

FIG. 34 is a model view showing the output of the sensor with a solid line in a dynamic abnormal state where the impeller vibrates greatly in its axial direction. A two-dot chain line of FIG. 34 shows an integrated value of the output voltage of the non-inverting terminal of the operational amplifier OP3. When the voltage (two-dot chain line) of the non-inverting terminal of the operational amplifier OP3 exceeds the threshold B, it is determined that the magnetic bearing is abnormal As the value of the output of the sensor to be used as the information for the detector for detecting abnormality in the control of the magnetic bearing, it is possible to use an addition of output values in a predetemiined period of time, an average of an addition of the output values in a predetermined period of time, and an average of the output values in a predetermined period of time.

In the case where the addition of output values of the sensor in a predetermined period of time is used, digital processing is used. In the case where the average of the addition of the output values of the sensor in a predetermined period of time is used, digital processing is also use In the case where the average of the output values of the sensor in a predetermined period of time is used, an analog circuit using a low-pass filter or digital processing can be also used.

It is preferable that the control device 206 has a function of determining whether the magnetic bearing is abnormal (second function of determining whether magnetic bearing is abnormal, function of determining whether electric current applied to magnetic bearing is abnormal). The function of determining whether the magnetic bearing is abnormal determines that the magnetic bearing is abnormal when the value of electric current detected by the function of monitoring the electric current applied to the electromagnet becomes more than a second predetermined value.

Figure 35:
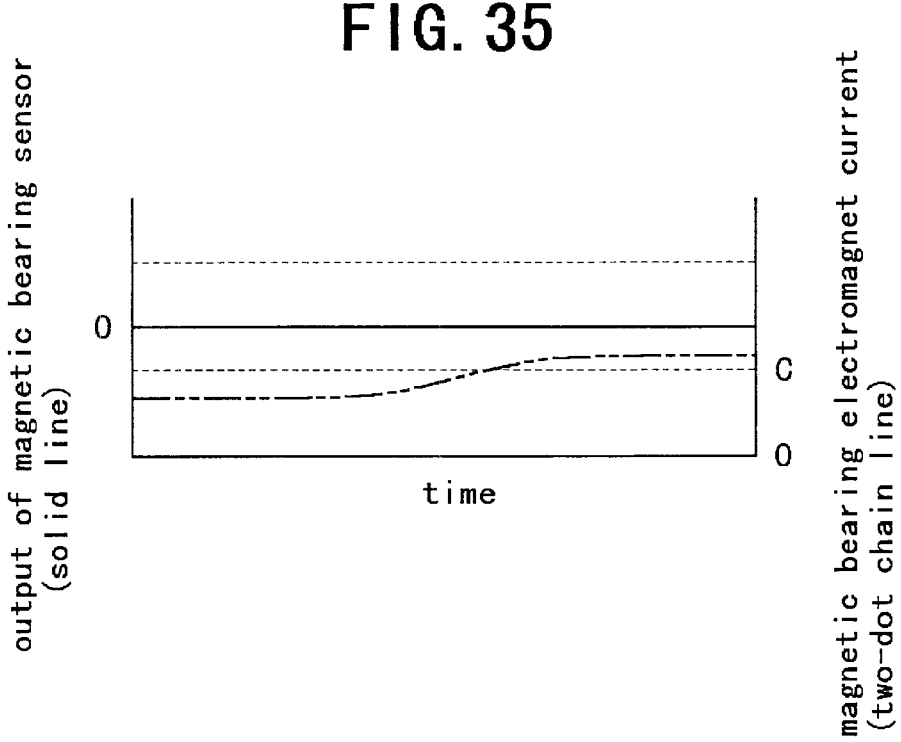
FIG. 35 is an explanatory view for explaining the relationship between time and an output of a magnetic bearing sensor as well as a value of electric current flowing through the electromagnet when the magnetic bearing is abnormal (abnormality of electric current flowing through electromagnet) in the centrifugal fluid pump assembly.

FIG. 35 is an explanatory view for explaining the relationship between time and the output of the magnetic bearing sensor as well as the value of electric current flowing through the electromagnet when the magnetic bearing is abnormal (abnormality of electric current flowing through electromagnet) in the pump assembly. As shown in FIG. 35, when thrombus is formed in the gap between the impeller and the housing at the electromagnet side thereof, the value of the electric current flowing through the electromagnet may increase even though the output of the sensor does not change. Thus, when the electric current flowing through the electromagnet becomes more than the threshold, it is determined that the magnetic bearing is abnormal (electric current applied to magnetic bearing is abnormal).

Figure 36:
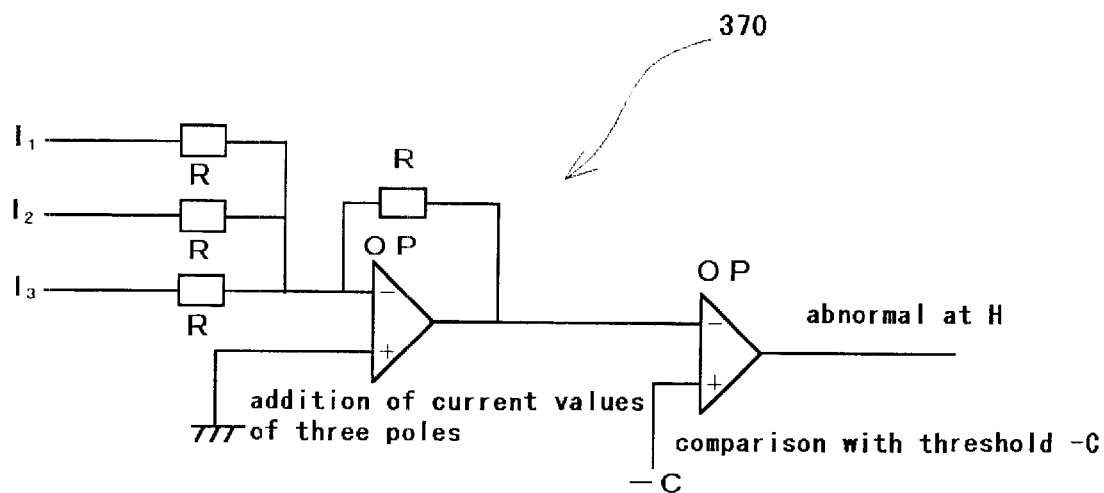
FIG. 36 is a block diagram showing an example of a detection circuit, for detecting abnormality (abnormality of electric current flowing through electromagnet) of the magnetic bearing, for use in the centrifugal fluid pump assembly of the invention.

As a detector 264 for detecting abnormality of electric current applied to the magnetic bearing to determine whether or not the magnetic bearing is abnormal, a circuit 370 as shown in FIG. 36 can be preferably used. FIG. 36 is a block diagram showing an example of a detection circuit for detecting abnormality of the magnetic bearing (abnormality of electric current flowing through electromagnet) for use in the plump assembly of the invention.

In the circuit 370, current values (I 1, I 2, I 3) corresponding to respective electromagnets (three in the embodiment) of the centrifugal pump for the magnetic bearing are monitored. When the sum of the values of the current values is larger than a threshold C, it is determined that the magnetic bearing is abnormal. More specifically, the first operational amplifier adds the current values (I 1, I 2, I 3) to each other, and the second operational amplifier compares the stun of the current values (I 1, I 2, I 3) with the threshold C. If the output of the second operational amplifier is H (when input value is smaller than threshold, output is H), it is determined that the magnetic bearing is abnormal. The detector for detecting the abnormality of the magnetic coupling is not limited to the circuit 370. For example, it is possible to use a detector that detects abnormality of the magnetic coupling when any one or two or more of the electric currents flowing through the electromagnet are larger than the threshold. Instead of the detector of the analog type, a detector of digital type may be used. As the value of electric current that is used as determining information in the detector for detecting abnormality of the electric current applied to the magnetic bearing, it is possible to use an addition of electric current in a predetermined period of time, an average of the addition of electric current in a predetermined period of time, and an average of the electric current in a predetermined period of time.

In the case where the addition of electric current values in a predetermined period of time is used, digital processing is used. In the case where the average of the addition of the electric current values in a predetermined period of time is used, digital processing is also used. In the case where the average of the electric current values in a predetermined period of time is used, an analog circuit using a low-pass filter or digital processing can be also used.

It is preferable that the control device 206 has a function of detecting temperature therein. hi the embodiment, the control device 206 has a detector 266 for detecting abnormality of the temperature therein to perform the function of detecting the temperature therein. The detector 266 for detecting the abnormality of the temperature therein is composed of temperature detection elements such as a thermistor and a thermocouple. When a temperature higher than 60° C. is detected, it is determined that the temperature in the control device is abnormal.

The control device 206 has an alarm output device 259 that operate when the above-described determining functions determine that an abnormality has occurred. The alarm output device 259 outputs alarm in different modes, depending on the kind of abnormality determined by the determining function. Supposing that the alarm output device 259 gives a sound, it is preferable that the level of the sound decreases, depending on the items determined as abnormal by the determining functions: When it is determined that the impeller has the power swing (in other words, when it is determined that magnetic coupling has power swing), the alarm output device 259 gives a highest alarm sound. when it is determined that the motor rotates in a high load-applied state, the alarm output device 259 gives a second highest alarm sound. When it is determined that the position of the impeller is abnormal (first magnetic bearing is abnormal), the alarm output device 259 gives a third highest alarm sound. When it is determined that the electric current applied to the magnetic bearing is abnormal (second magnetic bearing is abnormal), the alarm output device 259 gives a fourth highest alarm sound. when it is determined that the temperature in the control device is abnormal, the alarm output device 259 gives a fifth highest alarm sound. The level of the alarm sound can be changed by sound volumes, frequencies, periods, kind of alarm sound or combination thereof. It is preferable to establish priority on the abnormalities so that when a plurality of abnormalities is detected simultaneously, alarms are outputted in order of the priority. The above-described priority on the abnormalities is determined according to the degree of influence on the human body.

As the means for outputting an alarm when an abnormality has occurred, in addition to the use of a buzzer sound, it is possible to display an abnormal situation on a display provided on the control device or the like, put on an error lamp, use speaking by means of a voice function. In this case, it is also preferable to establish priority on the abnormalities to cope with abnormal situations.

According to the pump assembly of the invention, it is possible to reliably the occurrence of the power swing that prevents feeding of a liquid, which is the most serious abnormality in the centrifugal pump. Further, it is seldom for the function of determining whether or not the power swing has occurred to erroneously determine a state in which the power swing has not occurred as a state in which the power swing has occurred.

While the present invention has been described with reference to preferred embodiments thereof, it is to be understood that the invention is not limited to the disclosed embodiments or construction. On the contrary, the invention is intended to cover various modifications and equivalent arrangements included within the spirit and scope of the appended claims.

Although some preferred embodiments have been described, many modifications ad variations may be made thereto in the light of the above teachings. It is therefore to be understood that within the scope of the appended claims, the invention may be practiced otherwise than as specifically described

What is claimed is:

1. A centrifugal fluid pump assembly comprising
a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and
a control device having an input portion for inputting a set number of rotations of the motor or an input portion for inputting a set motor-driving current value; and a function of limiting an input of a number of rotations of the motor more than a predetermined number of rotations or limiting an input of the motor-driving current having a value more than a predetermined value.

2. A centrifugal fluid pump assembly according to claim 1, wherein the control device has the input portion for inputting a set number of rotations of the motor and a motor rotation control part having a function of storing an upper limit value of the motor-driving current and a function of limiting an input of the set motor-driving current having a value more than the stored upper limit value thereof.

3. A centrifugal fluid pump assembly according to claim 1, wherein the control device has the input portion for inputting a set number of rotations of the motor and a motor rotation control part having a function of storing an upper limit of the number of rotations of the motor and a function of limiting an input of a set number of rotations of the motor more than the stored upper limit value thereof.

4. A centrifugal fluid pump assembly according to claim 1, wherein the control device has an input mode selection part for selecting an input of the set motor-driving current value or an input of the set number of rotations of the motor.

5. A centrifugal fluid pump assembly comprising
a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device having an input portion for inputting a motor-driving current value or an input portion for inputting a set number-of-rotations of the motor; and a motor rotation control part having a function of storing an upper limit value of the motor-driving current and a function of limiting a supply of the motor-driving current having a value more than the stored upper limit value to the motor.

6. A centrifugal fluid pump assembly according to claim 5, wherein the function of limiting a supply of the motor-driving current having a value more than the stored upper limit value to the motor includes;

a function of comparing a stored upper limit value with a motor-driving current value inputted at the input portion for inputting a set motor-driving current value or with a motor-driving current value necessary for driving the motor at a number of rotation of the motor inputted at the input portion for inputting a set number-of-rotations of the motor; and a motor rotation control function of controlling a rotation of the motor such that the motor rotates at an inputted motor-driving current value if the inputted motor-driving current value is less than the upper limit value of the motor-driving current and of controlling the rotation of the motor such that the motor rotates at the upper limit value of the motor-driving current if the inputted motor-driving current value is more than the stored upper limit value.

7. A centrifugal fluid pump assembly according to claim 5, wherein the function of limiting a supply of the motor-driving current having a value more than the stored upper limit value to the motor has a current limiter circuit for preventing electric current having a value more than the upper limit value of the motor-driving current value from being outputted to the motor.

8. A centrifugal fluid pump assembly according to claim 7, wherein the function of limiting a supply of the motor-driving current having a value more than the stored upper limit value to the motor has the current limiter circuit and a comparator comparing the upper limit value of the motor-driving current outputted from the current limiter circuit with the motor-driving current value and outputting a smaller current value.

9. A centrifugal fluid pump assembly comprising a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including an input portion for inputting a set number of rotations of the motor and a motor rotation control part having a function of storing an upper limit of the number of rotations of the motor; a comparing function of comparing the stored upper limit of the number of rotations of the motor with a set number of rotations of the motor inputted at the input portion for inputting a set number of rotations of the motor; and a motor rotation control function of controlling a rotation of the motor such that the motor rotates at the set number of rotations of the motor if the set number of rotations of the motor is smaller than the upper limit of the number of rotations of the motor and such that the motor rotates at the upper limit of the number of rotations of the motor if the set number of rotations of the motor is more than the upper limit value thereof.

10. A centrifugal fluid pump assembly comprising a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a detecting portion for detecting the number of rotations of the motor and a motor rotation control part having a function of storing an upper limit of number of rotations of the-motor and a control function of controlling a rotation of the motor such that a detected number of rotations of the motor does not exceed the upper limit of the number of rotations.

11. A centrifugal fluid pump assembly comprising a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring function of monitoring electric current flowing through the electromagnet and a motor control function of controlling a rotation of the motor such that a rotational speed of the motor is reduced when an amplitude of electric current, flowing through the electromagnet, detected by the current monitoring function is more than a predetermined value.

12. A centrifugal fluid pump assembly comprising a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring function of monitoring electric current flowing through the electromagnet and a motor control function for controlling a rotation of the motor such that a rotational speed of the motor is reduced when an average of values of the electric currents flowing through the electromagnet detected by the monitoring function in a predetermined period of time is less than a predetermined value.

13. A centrifugal fluid pump assembly comprising a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring -function of monitoring electric current flowing through the electromagnet, a function for computing a average of the values of initial-time electric currents flowing through the electromagnet in the early period of time after an actuation of the centrifugal pump, a function for continuously computing a average of current-time values of the electric currents flowing thlough the electromagnet, a function for computing a fall degree of the average of the values of the electric by using the average of values of the initial-time electric currents and the average of values of the current-time electric currents and a motor control function for controlling a rotation of the motor such that a rotational speed of the motor is reduced when the fall degree of the average of the exceeds a predetermined range.

14. A centrifugal fluid pump assembly according to claim 1, wherein the control device has alarm means informing that the rotational speed of the motor controlled by the motor control function has decreased.

15. A centrifugal fluid pump assembly according to claim 1, wherein the impeller position control section has a plurality of electromagnets for attracting the second magnetic number of the impeller thereto and a plurality of position sensors for detecting the position of the magnetic member of the impeller.

16. A centrifugal fluid pump assembly according to claim 1, wherein the impeller position control section has a computing circuit for detecting the position of the second magnetic member of the impeller by means of a waveform of electric current flowing through the electromagnet.

17. A centrifugal fluid pump assembly according to claim 1, wherein the centrifugal fluid pump assembly is a centrifugal blood pump assembly.

18. A centrifugal fluid pump assembly comprising a centrifugal fluid pump comprising a centrifugal fluid pump section including a housing having a blood inlet port and a blood outlet port and an impeller having a first magnetic material and a second magnetic material disposed thereof and accommodated for rotation in the housing and without contacting the housing to feed a fluid by a centrifugal force developed during its rotation, an impeller rotational torque generating section including a rotor having a magnet for attracting the first magnetic material of the impeller and a motor for rotating the rotor, and an impeller position control section having an electromagnet for attracting the second magnetic material of the impeller, and a control device including a monitoring function of monitoring electric current flowing through the electromagnet; a monitoring function of monitoring motor-driving current; a monitoring function of monitoring the number of rotations of the motor; and a function of determining whether or not the impeller has a power swing by utilizing a current value monitored by the monitoring function of monitoring the electric current flowing through the electromagnet, a value of the motor-driving current monitored by the monitoring function of monitoring the motor-driving current, and the number of rotations of the motor monitored by the monitoring function of monitoring the number of rotations thereof.

19. A centrifugal fluid pump assembly according to claim 18, wherein the function of determining whether or not the impeller has the power swing determines that the impeller has the power swing when a current value monitored by the function of monitoring the electric current flowing through the electromagnet is less than a first predetermined value or when the value of the motor-driving current monitored by the function of monitoring the motor-driving current is lower than a first predetermined motor-driving current value corresponding to the number of rotations of the motor monitored by the function of motoring the number of rotations thereof.

20. A centrifugal fluid pump assembly according to claim 19, wherein the function of determining whether or not the impeller has the power swing stores a relational expression, between the number of rotations of the motor and the value of the motor-driving current, which is used to determent whether or not the impeller has the power swing.

21. A centrifugal fluid pump assembly according to claim 18, wherein the function of determining whether or not the impeller has the power swing uses an average of the current values in a predetermined period of time monitored by the function of monitoring the electric current flowing through the electromagnet.

22. A centrifugal fluid pump assembly according to claim 18, wherein the control device has a power swing cancellation function of temporary stopping type of suspending and resuming a rotation of the motor after the function of determining whether the impeller has a power swing has determined that the impeller has the power swing.

23. A centrifugal fluid pump assembly according to claim 18, wherein the control device a power swing cancellation function of a temporary low-speed type of rotating the motor at a low speed for a predetermined period of time and then increasing the number of rotations of the motor after the function of determining whether the impeller has a power swing g has determined that the impeller has the power swing.

24. A centrifugal fluid pump assembly according to claim 18, wherein the control device has a function of determining whether the motor rotates in a high load-applied state; and the function of determining whether the motor rotates in a high load-applied state determines that the motor rotates in a high load-applied state when a value of the motor-driving current monitored by the function of motor-driving the value thereof is larger than a second predetermined motor-driving current value corresponding to the number of rotations of the motor monitored by the function of monitoring the number of rotations thereof.

25. A centrifugal fluid pump assembly according to claim 24, wherein the function of determining whether the motor rotates in a high load-applied state stores a relational expression, between the number of rotations of the motor and the value of the motor-driving current, which is used to determine whether the motor rotates in a high load-applied state.

26. A centrifugal fluid pump assembly according to claim 13, wherein the control device has a function of monitoring an output value of an impeller position sensor and a function of determining whether a position of the impeller is abnormal; and the function of determining whether the position of the impeller is abnormal determines that the position of the impeller is abnormal when an output value of the function of monitoring the output value of the impeller position sensor is more than a first predetermined stored value or less than a second predetermined stored value.

27. A centrifugal fluid pump assembly according to claim 26, wherein the function of determining whether the position of the impeller is abnormal uses an average of the output values in a predetermined period of time monitored by the function of monitoring an output value of an impeller position sensor.

28. A centrifugal fluid pump assembly according to claim 18, wherein the control device has a function of determining whether a magnetic bearing is abnormal; and the function of determining whether the magnetic bearing is abnormal determines that the magnetic bearing is abnormal when the value of electric current detected by the function of monitoring electric current flowing through the electromagnet is more than a second predetermined value.

29. A centrifugal fluid pump assembly according to claim 18, wherein a function of determining whether a magnetic bearing is abnormal determines the magnetic bearing is abnormal when an average of values of electric currents in a predetermined period of time monitored by the function of monitoring electric current flowing through the electromagnet is more than the second predetermined value.

30. A centrifugal fluid pump assembly according to claim 18, wherein the control device has a function of detecting temperature therein.

31. A centrifugal fluid pump assembly according to claim 18, wherein the control device has an alarm output device that operates when it is determined by any one of the determining functions that abnormality has occurred.

32. A centrifugal fluid pump assembly according to claim 31, wherein the alarm output device outputs alarms in different modes, depending on the kind of abnormality determined by the determining function.

* * * * *

UNITED STATES PATENT AND TRADEMARK OFFICE
CERTIFICATE OF CORRECTION

PATENT NO.     : 6,398,506 B1
DATED          : June 4, 2002
INVENTOR(S)    : Jun Maekawa et al.

It is certified that error appears in the above-identified patent and that said Letters Patent is hereby corrected as shown below:

Column 11,
Line 9, delete "Tis" and insert -- This --.
Line 41, delete "Current" and insert -- current --.

Column 13,
Line 30, delete "Tile" and insert -- the --.

Column 14,
Line 11, delete "pluiip" and insert -- pump --.
Line 35, delete ".fmction" and insert -- function --.
Line 43, delete "pemussitle" and insert -- permissible --.
Line 50, delete "motor-drivilg" and insert -- motor-driving --.
Line 55, delete "cuiient" and insert -- current --.
Line 55, delete "theretluough" and insert -- therethrough --.

Column 20,
Line 46, delete "pimp" and insert -- pump --.

Column 22,
Line 67, delete "shroud" and insert -- shrouds --.

Column 24,
Line 21, delete "when" and insert -- When --.

Column 33,
Line 17, delete "Rd." and insert -- R1. --.
Line 60, after "OP3" insert -- . --.
Line 60, delete "when" and insert -- When --.

Column 39,
Line 31, delete "-" between "monitoring" and "function".

UNITED STATES PATENT AND TRADEMARK OFFICE
CERTIFICATE OF CORRECTION

PATENT NO.     : 6,398,506 B1
DATED          : June 4, 2002
INVENTOR(S)    : Jun Maekawa et al.

It is certified that error appears in the above-identified patent and that said Letters Patent is hereby corrected as shown below:

<u>Column 41,</u>
Line 15, delete "13" and insert -- 18 --.

Signed and Sealed this

Fourth Day of March, 2003

JAMES E. ROGAN
*Director of the United States Patent and Trademark Office*